(12) United States Patent
Kronestedt et al.

(10) Patent No.: US 9,011,386 B2
(45) Date of Patent: Apr. 21, 2015

(54) DEVICE FOR DELIVERING MEDICAMENT

(75) Inventors: Victor Kronestedt, Stockholm (SE);
Lennart Brunnberg, Tyresö (SE);
Stephan Olson, Stockholm (SE);
Anders Karlsson, Saltsjö-Boo (SE);
Tomas Deurell, Årsta (SE)

(73) Assignee: SHL Group AB, Nacka Strand (SE)

( * ) Notice: Subject to any disclaimer, the term of this patent is extended or adjusted under 35 U.S.C. 154(b) by 2696 days.

(21) Appl. No.: 11/282,593

(22) Filed: Nov. 21, 2005

(65) Prior Publication Data
US 2006/0276754 A1 Dec. 7, 2006

Related U.S. Application Data

(63) Continuation-in-part of application No. 11/140,989, filed on Jun. 1, 2005, now abandoned.

(51) Int. Cl.
*A61M 5/178* (2006.01)
*A61M 5/20* (2006.01)
*A61M 15/00* (2006.01)
*A61M 5/24* (2006.01)
(Continued)

(52) U.S. Cl.
CPC . *A61M 5/20* (2013.01); *A61M 5/24* (2013.01); *A61M 5/2448* (2013.01); *A61M 5/3146* (2013.01); *A61M 5/31535* (2013.01); *A61M 5/31551* (2013.01); *A61M 5/31553* (2013.01); *A61M 5/31556* (2013.01); *A61M 5/3156* (2013.01); *A61M 5/31573* (2013.01); *A61M 5/31583* (2013.01); *A61M 5/31593* (2013.01); *A61M 15/0045* (2013.01); *A61M 15/0065* (2013.01); *A61M 15/0091* (2013.01); *A61M 2005/2013* (2013.01); *A61M 2005/202* (2013.01); *A61M 15/0076* (2013.01)

(58) Field of Classification Search
USPC ......... 604/131, 134–139, 220–224, 228, 229, 604/186, 206
See application file for complete search history.

(56) References Cited

U.S. PATENT DOCUMENTS

| | | | | |
|---|---|---|---|---|
| 1,718,596 A | * | 6/1929 | Smith | 604/223 |
| 3,494,358 A | * | 2/1970 | Duesterheft et al. | 604/137 |
| 5,114,406 A | * | 5/1992 | Gabriel et al. | 604/136 |

(Continued)

FOREIGN PATENT DOCUMENTS

| | | |
|---|---|---|
| DE | 100 61 723 | 7/2002 |
| EP | 0 666 084 | 8/1995 |

(Continued)

*Primary Examiner* — Nicholas Lucchesi
*Assistant Examiner* — Gerald Landry, II
(74) *Attorney, Agent, or Firm* — Piedmont Intellectual Property

(57) ABSTRACT

The present invention relates to a device for the delivery of predetermined doses of liquid medicament to a patient, which medicament is intended to be inhaled by the patient or intended to be injected into the body of the patient. The device is adapted to be in a medicament delivery state and in a medicament non-delivery state. When the device is in a medicament delivery state, said device is adapted to drive a piston into a cartridge containing the liquid medicament to be delivered, with a force that is above or equal to a predetermined minimum force value and below a predetermined maximum force value. The minimum force value is the lowest force value needed to deliver the predetermined dose and the maximum force value is the first force value at which it exists a risk of damaging the cartridge or the components of the device.

19 Claims, 13 Drawing Sheets

(51) Int. Cl.
*A61M 5/31* (2006.01)
*A61M 5/315* (2006.01)

(56) References Cited

U.S. PATENT DOCUMENTS

| | | | |
|---|---|---|---|
| 5,279,586 A * | 1/1994 | Balkwill | 604/207 |
| 5,320,609 A * | 6/1994 | Haber et al. | 604/135 |
| 5,478,316 A | 12/1995 | Bitdinger et al. | |
| 5,514,097 A * | 5/1996 | Knauer | 604/136 |
| 6,042,571 A * | 3/2000 | Hjertman et al. | 604/208 |
| 6,221,046 B1 * | 4/2001 | Burroughs et al. | 604/153 |
| 6,475,193 B1 | 11/2002 | Park | |
| 6,673,035 B1 * | 1/2004 | Rice et al. | 604/72 |
| 2001/0053893 A1 * | 12/2001 | Larsen | 604/207 |
| 2002/0120235 A1 * | 8/2002 | Enggaard | 604/135 |
| 2004/0210199 A1 * | 10/2004 | Atterbury et al. | 604/224 |
| 2006/0178638 A1 * | 8/2006 | Reynolds | 604/191 |
| 2006/0206057 A1 * | 9/2006 | DeRuntz et al. | 604/224 |
| 2006/0276753 A1 * | 12/2006 | Kronestedt et al. | 604/186 |
| 2009/0054839 A1 * | 2/2009 | Moller et al. | 604/135 |

FOREIGN PATENT DOCUMENTS

| | | |
|---|---|---|
| WO | WO 01/87384 | 11/2001 |
| WO | WO 02/053214 | 11/2002 |
| WO | WO 2004/028598 | 4/2004 |

* cited by examiner

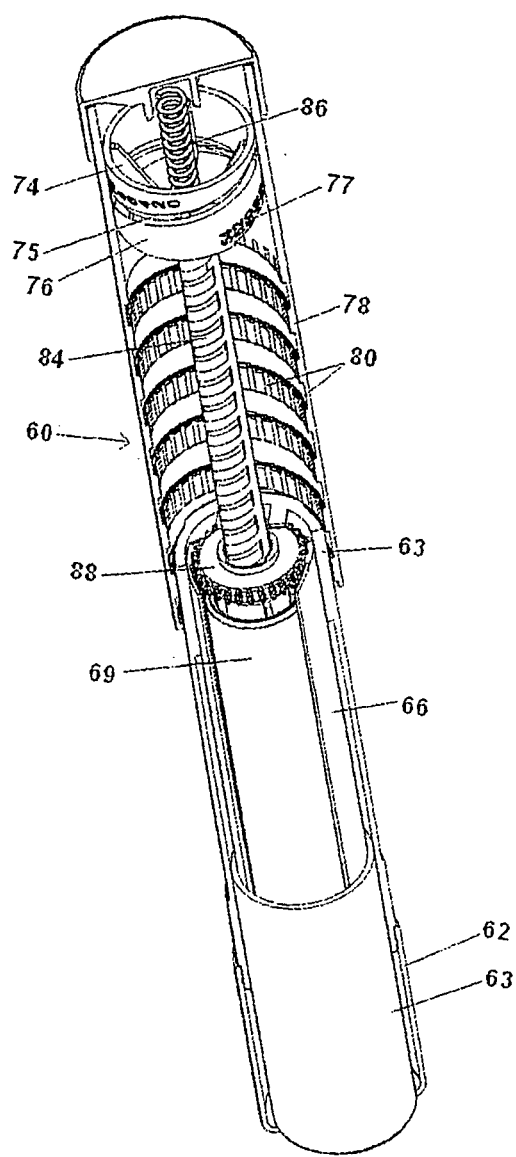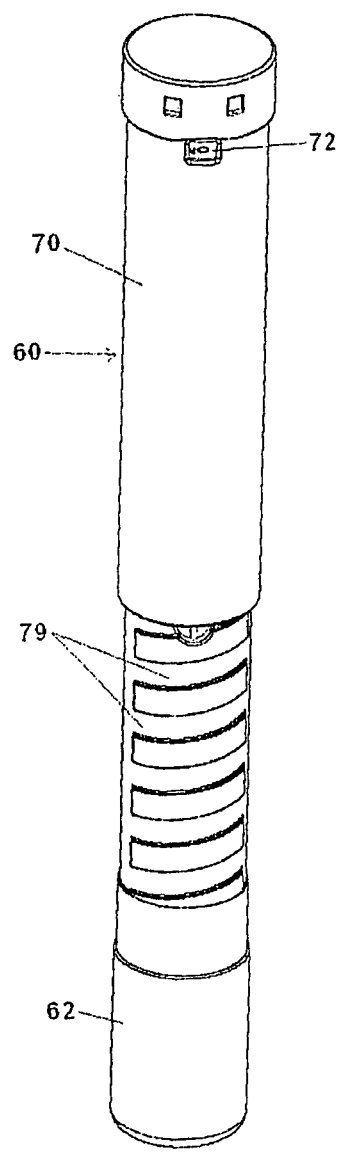
Fig. 12
Fig. 13

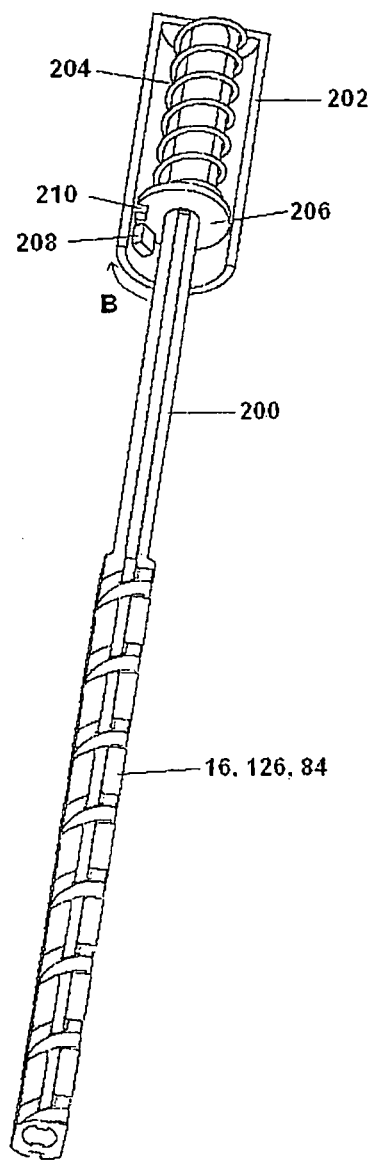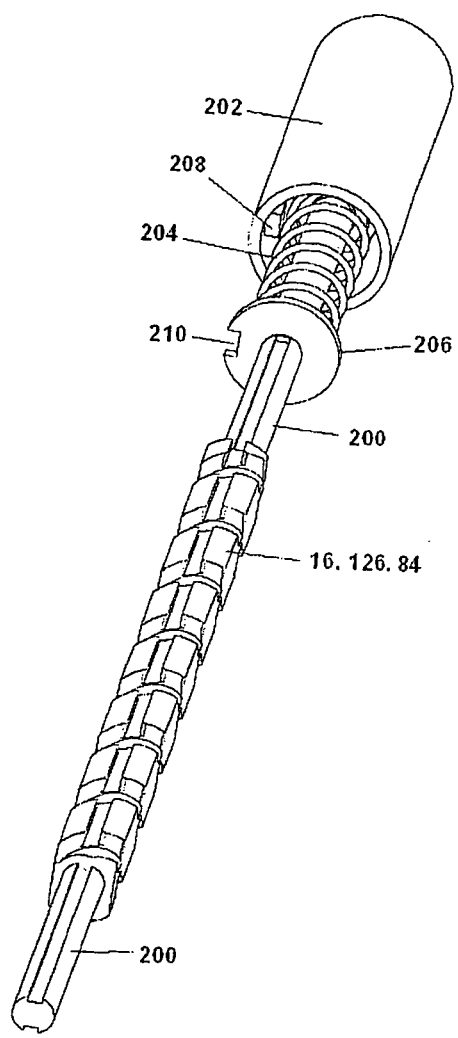
Fig. 16                    Fig. 17

DEVICE FOR DELIVERING MEDICAMENT

TECHNICAL FIELD

The present invention relates to a device for the delivery of predetermined doses of liquid medicament to a patient, which medicament is intended to be inhaled by the patient or intended to be injected into the body of the patient. The device is adapted to be in a medicament delivery state and in a medicament non-delivery state. When the device is in a medicament delivery state, said device is adapted to drive a piston into a cartridge containing the liquid medicament to be delivered, with a predetermined force value. Said force is preferably above or equal to a predetermined minimum force value and below a predetermined maximum force value.

BACKGROUND ART

The development of devices for delivering liquid medicament to a patient, have during the recent years become more and more directed towards the ability for the patient themselves to administer the medicament with a predetermined dose in an easy, safe and reliable way and also to facilitate the administration of medicaments for hospital personnel in the same facilitated way. Depending on the intended use and type of medicament, they have developed a varying degree of automatic functions.

Currently existing automatic medicament delivery devices, conventionally comprise a cartridge or the like, containing the liquid medicament to be delivered. Said conventional delivery device is further provided with a plunger rod that is adapted to be in contact with a piston provided inside the cartridge. Upon delivery of the medicament contained in the cartridge, the plunger rod will exert a force upon the piston, whereupon the piston will move forward inside the cartridge and thus expel the medicament from the cartridge. The distance that the piston moves inside the cartridge, determines the amount of medicament to be delivered.

The force that is applied to the piston during medicament delivery, is generally accomplished by means of having a pre-tensed helical spring connected to the plunger rod and thus provided in the interior of the delivery device, wherein the force is obtained in accordance with Hooke's law (1):

$$F = -k^*y \quad (1)$$

wherein F is the force exerted by the spring (N), y is the displacement of the spring from its original position (m) and k is the spring constant (N/m).

From Hookes law follows that the force acting on the piston, will decline linearly as the piston moves forward in the cartridge. Thus, when a large volume of medicament is to be expelled from the cartridge, the force needs to be initially high in order to be able to move the piston all the way down to the required position of the piston in the cartridge. However, the conventional cartridge is often made of an easily breakable material, such as glass, and having an initial high force acting on the piston will result in that there is a substantial risk of damaging the cartridge, which is most undesirable.

Having for instance a high viscosity medicament contained in the cartridge or having a fine needle attached to the delivery device, will also require a higher force to act on the piston. The same applies for situations when the medicament is to be delivered within a short period of time. One can generally say that when a plunger rod is allowed to freely act on the piston, there is a substantial risk of damaging the cartridge when the piston is applied with a force that is above or equal to approximately 50-60 N.

One solution to the problem is to provide the delivery device with a spring having a smaller spring constant, i.e. the gradient in the force-way diagram will have more flat appearance and the initial force acting on the piston will be decreased. However, a smaller spring constant would require a larger spring and hence a larger device. A larger device is generally not handled as easily as a device with a smaller size. Another problem is, that there is a minimum force value required to initially act on the piston in order for the piston to start the movement from its original position in the distal end of the cartridge, which minimum force in the art often is referred to as the "break loose force". This force would not be obtained if the device was provided with a spring having a too small spring constant.

Also, the force acting on the piston is higher during the beginning of the medicament delivery procedure than towards the end, which results in that the piston moves faster in the beginning than in the end of said procedure, i.e. the medicament is during the procedure delivered to the patient at a higher rate in the beginning than in the end. This is undesirable, especially when the medicament is to be inhaled by the patient. This phenomena also results in that the rate with which the medicament is delivered may differ from one dose to another, since a higher dose requires an initially higher force to act on the piston than a lower dose, i.e. the so called "dose-to-dose accuracy" is poor with prior art automatic delivery devices.

Moreover, the conventional cartridge does not always have a smooth interior surface but may exhibit irregularities or unevenness as a result from the manufacturing procedure or as a result from the lubrication procedure, since the interior of the conventional cartridge most often is lubricated before use, for instance by the use of silicon oil. Such an irregularity or unevenness may increase the travel resistance acting on the piston which may cause the piston to slow down or even get stuck before it has reached its predetermined position inside the cartridge, especially if the irregularity is to be found towards the end of the distance that the piston is required to travel when the force acting on it has declined to a low value. It is generally known in the art that the force acting on the piston should not be below approximately 5 N, which thus is the lowest sliding force value needed in order not to allow the piston to get stuck before the entire set dose has been delivered.

Another problem is that the conventional delivery devices are generally made of plastic material due to manufacturing and economical reasons. Having a pre-tensed spring provided in the interior of such a device, results in that the tension caused by the pre-tensed spring, is held back by means of plastic components, which can lead to creep and hence plastic deformation of the plastic materials. This may reduce the life of the device and affect its accuracy and may also affect the automatic delivery function of said device. Also, having a high force acting on the piston during medicament delivery can cause damage of the plastic components of the device, which thus is another reason why it is not suitable to have a too high force applied to the piston, besides the risk of damaging the cartridge.

It is also important that the user of the delivery device is able to set the amount of medicament that is to be delivered in an relatively easy and reliable way. Likewise it is important and highly desired that such a delivery device is able to target specific time limits, for instance a predetermined injection time or deliver a dose within a determined time range.

U.S. Pat. No. 5,478,316 (Bitdinger et al) describes a device for automatic injection of a material into the body. In order to avoid the high impact of prior art devices, the device is provided with a constant force spring for moving a syringe assembly with respect to a housing and towards the skin of the patient, and for urging a rod in the direction of a piston provided inside a cartridge. The force exerted by the constant force spring is said to be sufficient to overcome the friction between the piston and the cartridge and between the needle and the user's skin.

Even though U.S. Pat. No. 5,478,316 describes the avoidance of a high impact, the device disclosed is not provided with means in order to set the force exerted on the rod to a predetermined force value, thus the advantage of applying a force to the rod that is within a predetermined force range is not described. Moreover, the device is not provided with means in order to set a predetermined dose of medicament to be delivered.

SUMMARY OF THE INVENTION

The object of the present invention is therefore to provide an automatic liquid medicament delivery device, which during medicament delivery applies a force with a predetermined force value to a piston, which ensures that a predetermined volume of medicament is expelled from a cartridge.

The present invention also substantially lowers the risk of damaging the cartridge and/or the device during medicament delivery in comparison with prior art automatic liquid medicament delivery devices.

The inventive delivery device also substantially improves the dose and the dose-to-dose accuracy in comparison with prior art devices.

With the present invention it also possible to set the predetermined dose that is to be delivered in an easy and reliable way.

Another object of the present invention is to provide an automatic liquid medicament delivery device, which substantially reduces the problems with creep in and plastic deformation of the plastic materials of the delivery device.

With the inventive delivery device it is also possible to deliver the predetermined dose in multiple administration steps.

Yet another object with the present invention is to provide a method for using the delivery device.

These objects are accomplished with a delivery device according to the preamble of the independent claim(s) provided with the features according to the characterizing portions of the independent claim(s).

Preferred embodiments of the present invention are set forth in the dependent claims.

BRIEF DESCRIPTION OF THE DRAWINGS

FIG. 1 illustrates the delivery device in a cross-sectional view without the outer cover, FIG. 2 illustrates the distal part of the delivery device without the outer cover, the housing member and the coupling spring, FIG. 3 illustrates the delivery device as described in connection to FIG. 2 but including the housing member and the coupling spring, FIG. 4 illustrates the housing member and the flat spiral spring with the proximal end of the housing member facing towards the viewer, FIG. 5 illustrates the housing member and the flat spiral spring, comprised in a spring cover, with the distal end of the housing member facing towards the viewer, FIG. 6 illustrates the connection between the actuation sleeve, a plunger rod driving member and the plunger rod with the proximal end of the actuation sleeve facing towards the viewer, FIGS. 7-11 refer to the delivery device according to a second embodiment;

FIG. 12 illustrates the delivery device partly in cross-section,

FIG. 13 illustrates an elevation view of the device,

FIG. 16 illustrates the second rod in a first state, wherein the distal end of the second rod is comprised within a housing, FIG. 17 illustrates the second rod of FIG. 16 in a second state.

FIG. 20 illustrates a partly cross-sectional view of the distal part of the delivery device according to a configuration wherein the plunger rod is adapted to be in a rotating state during medicament delivery, FIG. 21 illustrates the plunger rod driving member from FIG. 20 from above.

DETAILED DESCRIPTION OF THE PREFERRED EMBODIMENTS OF THE PRESENT INVENTION

In the present application, when the term "distal part/end" is used, this refers to the part/end of the delivery device, or the parts/ends of the members thereof, which under use of the delivery device, is located the furthest away from the medicament delivery site of the patient. Correspondingly, when the term "proximal part/end" is used, this refers to the part/end of the delivery device, or the parts/ends of the members thereof, which under use of the delivery device, is located closest to the medicament delivery site of the patient.

The Delivery Device of the Present Invention According to a First Embodiment

The delivery device 2, comprises in its distal end a dose setting member in the form of a dose wheel 4 and in its proximal end a cartridge housing 8 comprising a cartridge 10. The cartridge 10 is intended to be filled with the liquid medicament to be administered to the patient and the delivery device is thus provided with means in order to be connected to a suitable medicament administrating member, provided with corresponding means (not shown). The medicament administrating member is preferably a mouth or nasal piece, which the patient puts in his mouth or nose, respectively, whereby a metered dose of medicament is inhaled by the patient when the delivery device is set in a medicament delivery state, which will be described in further detail below. The medicament administering member can also be a member that introduces the liquid medicament to the eye of the patient, such as a suitable nozzle that sprays the medicament to the eye, or a member that introduces the medicament to the eye in the form of droplets. Naturally, a nozzle as a medicament administrating member, can also be used in order to spray the medicament onto the skin of the patient. The medicament administrating member can also be a needle for the injection of a liquid medicament into the body of the patient, wherein the liquid can have a low as well a high viscosity.

Figure 2:
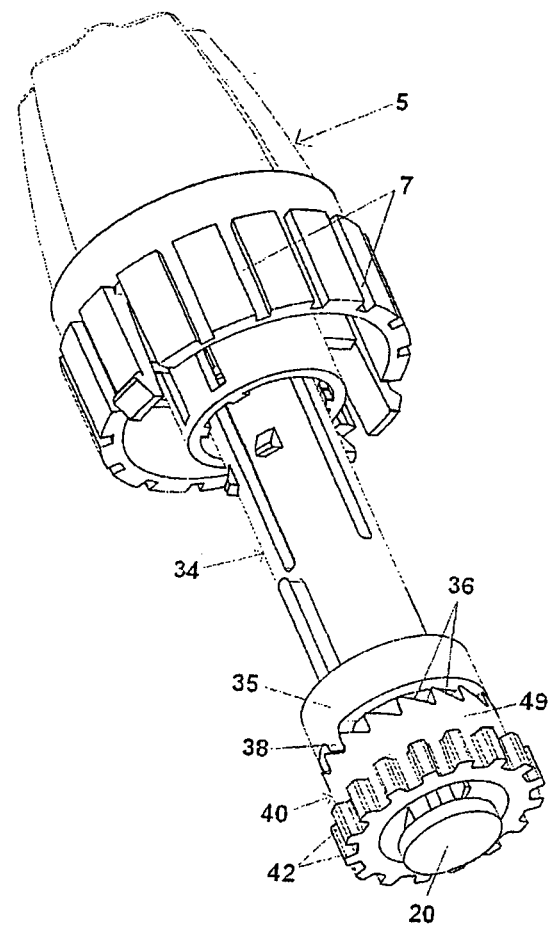
Figure 5:
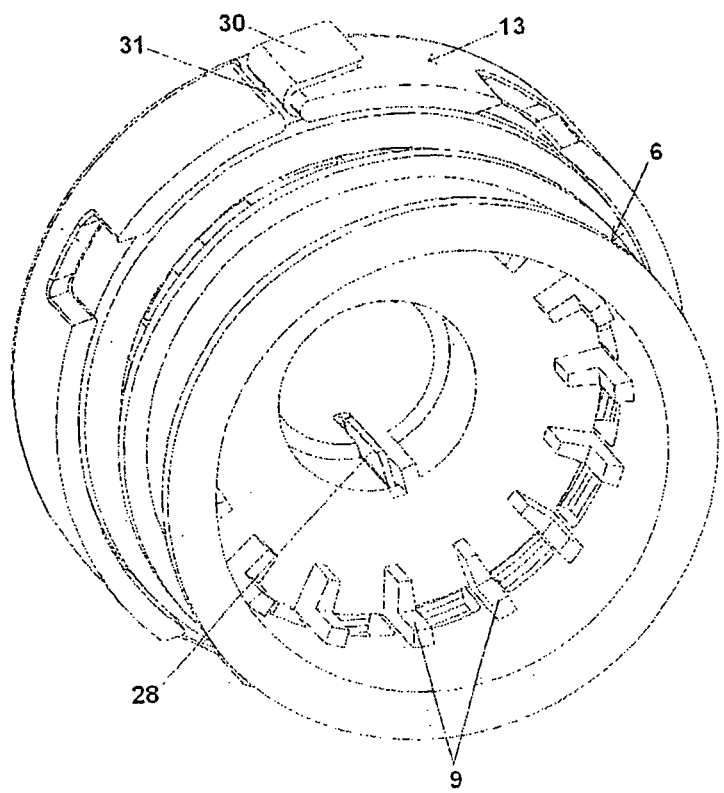

The dose wheel 4 comprises a dose wheel turning member 5 and a member 6 housing the energy accumulating member (see below), which members 5, 6 are adapted in order to be firmly, and removably, connected with each other. For this purpose, as seen in FIGS. 2 and 5, respectively, the exterior of the proximal part of the dose wheel turning member 5 is provided with a number of equally distributed splines 7, which are adapted to engage corresponding inward protruding means 9 of the housing member. Thus, when the splines 7 and the protruding means 9 are engaged, the housing member 6 is rotated along with the turning member 5, when the latter is rotated for instance clock-wise, which will be described in further detail below. When the turning member is pulled towards the distal end of the delivery device, the splines 7 and the protruding means 9 are brought out of engagement and the dose wheel turning member is thus adapted to also release the housing member. The housing member 6 is further provided with a shoulder 11 adapted to be in contact with a corresponding means (not shown) in the outer cover of the device (not shown).

An elongated screw threaded plunger rod 16 is provided in the interior of the delivery device 2, running along the longitudinal axis of said device 2, which device thus is provided with means in order to house such a screw threaded member 16. The plunger rod 16 is in its proximal end provided with a plunger cap 20 adapted to be in contact with a piston 22, which piston 22 is sealingly and slidably provided inside the cartridge 10.

The plunger rod 16 can be provided as a hollow member or a solid member. In the embodiment, wherein the plunger rod 16 is provided as a hollow member, a second rod 200 can be provided inside the hollow plunger rod 16, extending along the longitudinal axis of said rod. Said second rod 200 can be a hollow member or a solid member as well. In the embodiment, wherein the plunger rod 16 is provided as a solid member, this second rod 200 can provided so that its proximal end is in contact with the distal end of the plunger rod 16. In any case, the distal end of the second rod, preferably extends beyond the distal end of the device, which distal end of the device 2 thus is provided with an opening (not shown) in order to allow the second rod to extend beyond said end. The user of the device can thus manually apply a force, for instance by his hand, fingers or the like, on the distal end of the second rod 200, which thus provides for an additional force acting on the piston. This will be described in further detail below.

The distal end of the second rod 200 can also be comprised within in a rotatable second rod housing 202, as seen in FIGS. 16 and 17, respectively. The proximal end of the housing 202 is adapted to be firmly fixed, however adapted to be rotated, to the distal end of the delivery device 2. The proximal end of the housing 202 can for instance be in engagement with a corresponding groove (not shown) provided on the distal end of the device 2. A helical second rod spring 204 is provided around the distal end of the second rod. The distal end of the spring 204 is in contact with the inner surface of the distal end of the housing 202 and the proximal end of the spring 204 is in contact with a plate 206 firmly fixed to the second rod 200. The housing 204 is further provided with an inward protruding pin 208 that corresponds to a notch 210 in the plate 206.

When the housing is rotated, for instance in the direction as indicated by the arrow B in FIG. 16, the pin 208 will be provided just proximally of the notch 210, whereupon the spring 202, which prior to the rotation of the housing 202 is held in a compressed state, can expand and push the second rod towards the proximal end of the device, as seen in FIG. 17. FIGS. 16 and 17 thus illustrate a first and a second state of the second rod, respectively. The housing 202 can thereafter be pulled distally until the plate 206 is positioned distal to the pin 208, whereupon the housing is rotated until the pin 208 is in contact with the proximal surface of the plate 206. The second rod can also be provided with means (not shown) that prevents said rod from moving along its longitudinal axis and/or rotating after said rod have been urged towards the proximal end of the device. The second rod can also be provided with thread means in order to provide for a controlled movement of the rod. In FIGS. 16-17 is shown the embodiment wherein the second rod is provided in the hollow part of the plunger rod 16. However, it is to be understood that the proximal end of the second rod just as well can be in contact with the distal end of the plunger rod 16 as described above.

Optionally, a third rod, provided as a solid or a hollow member, can be provided in the delivery device, connected to the second rod with any of the means described above in connection with the coupling between the second rod and the plunger rod. The third rod can be provided with a rotating or linear moving locking mechanism or a threaded means, as described above in connection with the second rod. The function of the third rod will be described below.

Figure 4:
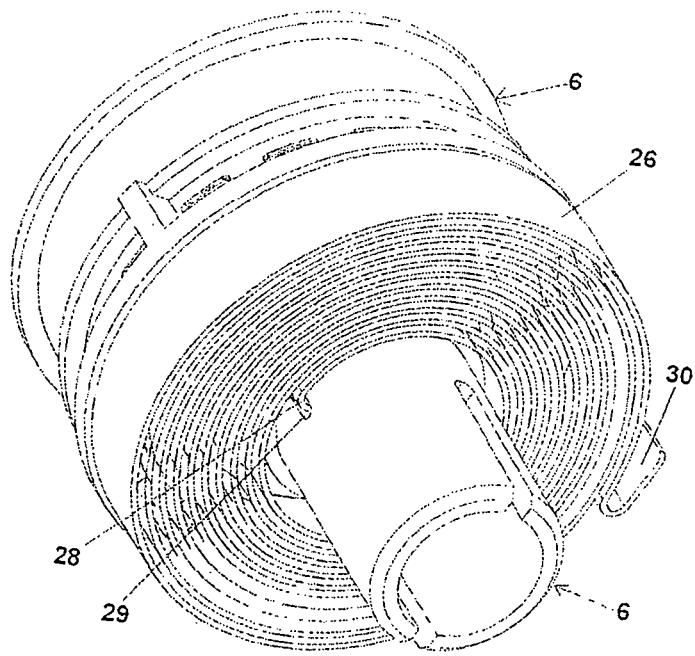

The housing member 6 is adapted to house an energy accumulating member in the form of a flat spiral spring 26, which spring 26 is provided winded in layers around the exterior of the proximal part of the housing member 6, as seen in FIG. 4. The flat spiral spring 26 is in its inner end provided with inner holding means in order to be attached to the housing member 6, such as for instance a protruding member 28 adapted to be fitted with a corresponding slit 29 in the housing member 6, or alternatively a hole of a suitable size in the flat spiral spring 26, and a smaller screw or other similar means for the anchoring of the flat spiral spring 26 in the housing member 6.

At the outer end of the flat spiral spring 26, said flat spiral spring 26 is provided with outer holding means in order to be connected to the flat spiral spring cover 13 of the delivery device 2. Said outer holding means comprises preferably a bend 30 of the outer end of the flat spiral spring 26, which hitches corresponding means 31 in the flat spiral spring cover 13. The cover 13 is provided with means (not shown) in order to be rotationally fixed in the outer cover.

Figure 3:
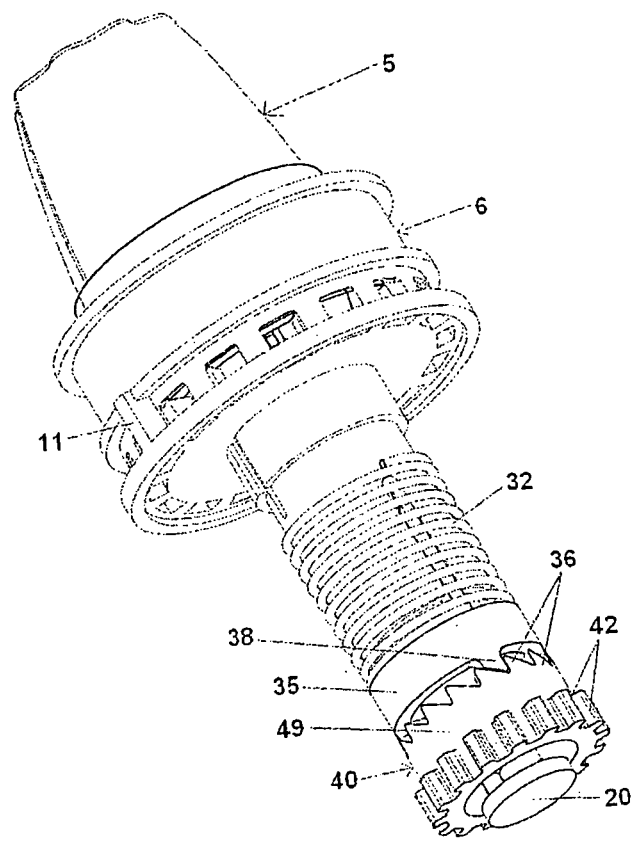

The dose wheel 4 is further in its proximal end adapted to house a coupling member 34, as seen in FIG. 2. Said coupling member is in its proximal end provided with a crown 35, which proximal end in turn is provided with at least one, preferably two equally distributed, bevelled protrusions 38. The crown 35 of the coupling member 34 is adapted to engage a plunger rod driving member, in the form of a nut 40. Herein the term nut is defined as a member provided with a through going hole, such that the interior of the member is provided with a thread of predetermined pitch of grooving, i.e. a predetermined screw pitch, said member is thus adapted to be screw threaded on a second member provided with a corresponding thread. The nut 40 is in this case adapted to engage with the plunger rod 16, i.e. the interior of the nut 40 is provided with grooves of a predetermined pitch in order to be screw threaded on the plunger rod 16. The nut 40 is designed as to in its proximal end be provided with outwardly protruding flanges 42 and in its distal end be provided with a skirt 49, the distal end of which is provided with a number of equally distributed bevelled recesses 36, which correspond to the protrusions 38 of the crown 35. The coupling member is further provided with a helical coupling spring 32, which proximal end is in contact with the distal end of the crown 35, as seen in FIG. 3. The distal end of the coupling spring 32 is firmly fixed to the coupling member.

Figure 1:
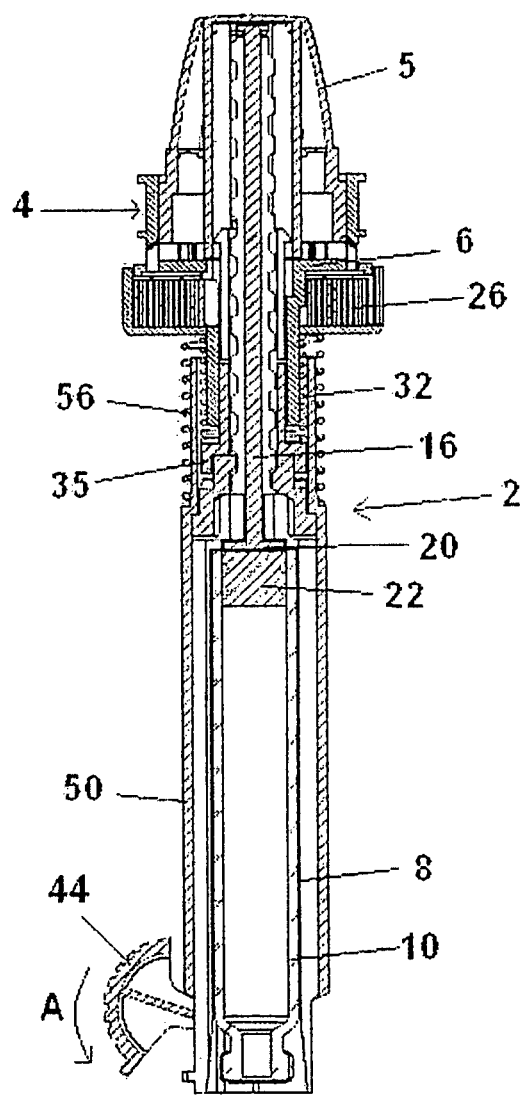
FIGS. 1-6, and 20-21 refer to the delivery device according to a first embodiment.
Figure 6:
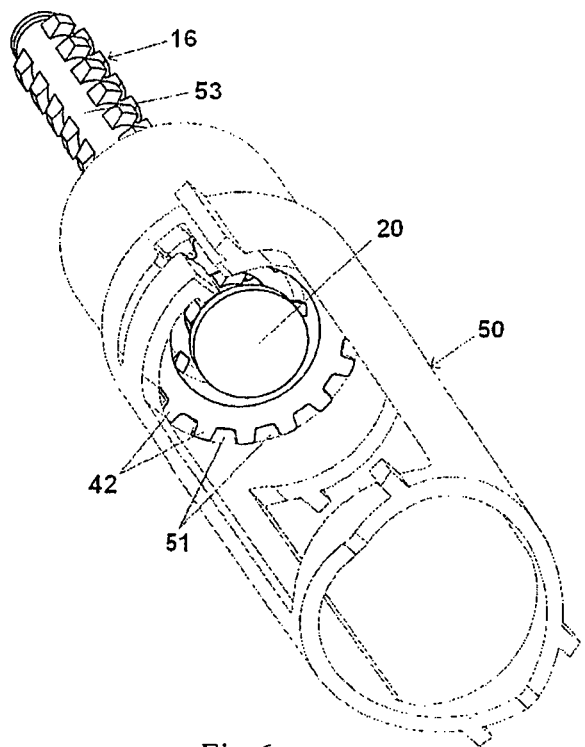

When the delivery device 2 of the first embodiment is in a locked state, i.e. a non-medicament delivery state, as will be described in further detail below, the nut 40 is held in a locked non-rotatable state by means of an actuation sleeve 50. The interior of said sleeve 50 is for this purpose provided with inward protruding stopper means 51, adapted to be provided in between the protruding flanges 42 of the nut 40, see FIG. 6. The actuation sleeve 50 is further adapted to, preferably at is proximal end, engage a dose actuation member 44, and is at its distal end provided with means in order to be connected to a helical actuation spring 56, said spring 56 is provided surrounding the distal end of the actuation sleeve and the distal end of the actuation spring 56 is in contact with the dose wheel 4, as seen in FIG. 1.

Figure 20:
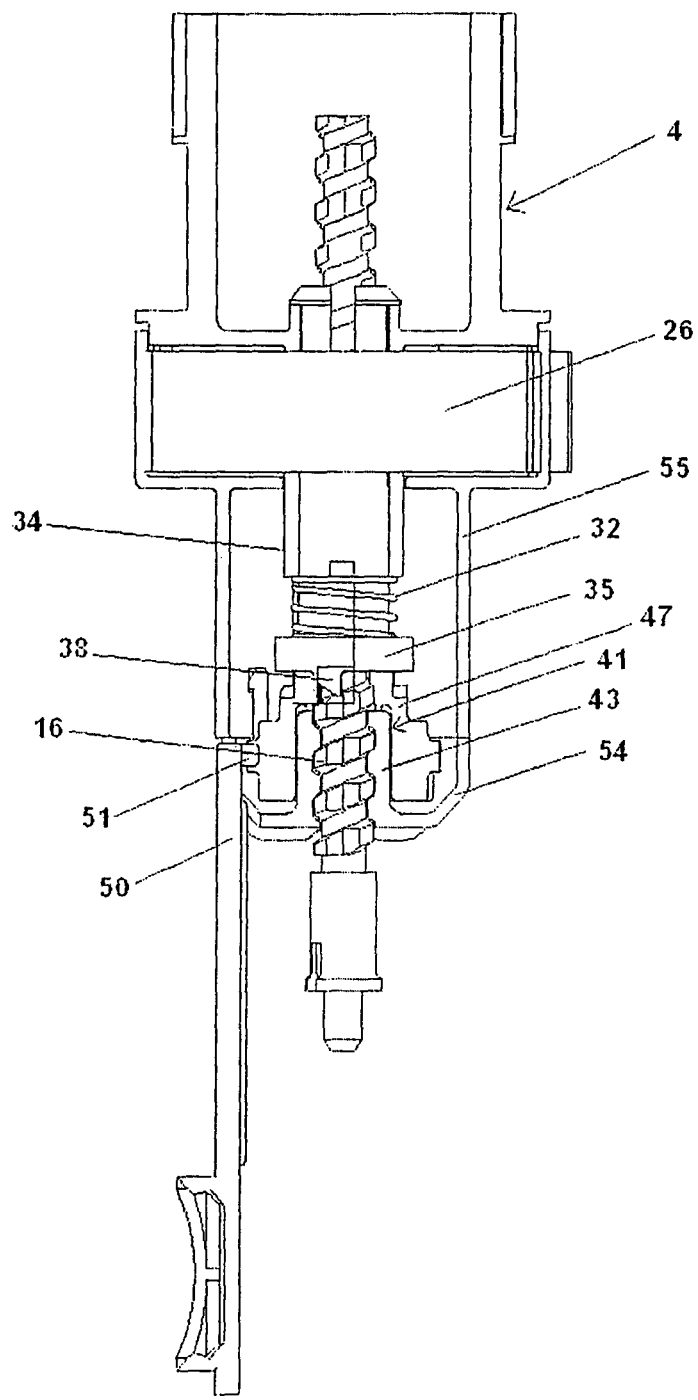
Figure 21:
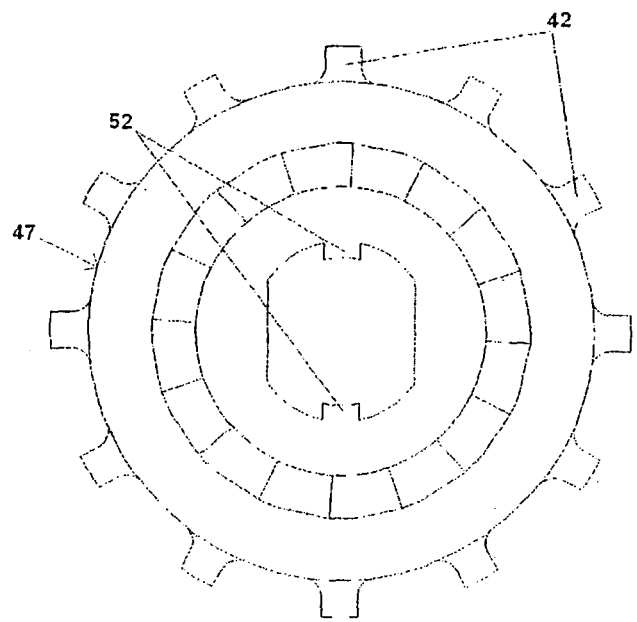

FIG. 20-21 refer to a configuration of the delivery device according to the first embodiment, wherein the plunger rod is adapted to be in a rotating state during medicament delivery. Hence, the above described refers to a configuration, wherein the plunger rod is adapted to be in a non-rotating state during medicament delivery. However, the two configurations coincide in most of their respects. The main difference between said configurations, is within the plunger rod driving member. This will be described in further detail below and also in connection with the preferred use of the delivery device according to the first embodiment.

In the plunger-rod-rotating-state-configuration of the delivery device 2, a non-rotating carrier 41 is partly provided in between a plunger rod driving member 47 and the plunger rod 16. In FIG. 20, the driving member 47 and the carrier 41 are seen in cross section which is not the case for the coupling member 34. Also in the plunger-rod-rotating-state-configuration, the bevelled protrusions 38 of the coupling member are adapted to abut against bevelled recesses 36 of the driving member 47. This is not seen in FIG. 20, due to the cross-sectional view of the member 47. However, even if not shown in FIG. 20, the plunger rod driving member 47 has a skirt 49 provided with recesses 36 just like the plunger rod driving member 40. The protrusions 38 and the recesses 36 are adapted to cooperate substantially in the same way also in the plunger-rod-rotating-state-configuration. That is, the distal part of the plunger rod driving member 47, has the same appearance and function as the plunger rod driving member 40 also in the plunger-rod-rotating-state-configuration.

However, in the plunger-rod-rotating-state-configuration, the through going hole provided in the plunger rod driving member 47, can be said to comprise two sections; a distal section and a proximal section, wherein the distal section has a diameter that is smaller than the diameter of the proximal section. The plunger rod driving member 47 thus comprises a distal part and a proximal part, corresponding to the distal and proximal sections, respectively, of the hole. The interior of the distal part of the plunger rod driving member 47 is provided with interior means 52, see FIG. 21, that are adapted to set the plunger rod in a rotating state, i.e. the means 52 corresponds to longitudinal extending means 53 on the rod 16. The means 52 are thus adapted to travel along the longitudinal axis of the rod 16. The interior of the proximal part of the driving member 47 is provided with a substantially flat surface. In the plunger-rod-rotating-state-configuration, only the distal part of the plunger rod driving member 47 is adapted to engage the plunger rod. The proximal part of the driving member 47 is adapted to house an interior part of the carrier 41.

The carrier 41 is a fix non-rotating member, having an interior tubular formed part 43 which is housed within the proximal part of the driving member 47. In between the outer surface of the tubular formed part 43 and the interior of the proximal part of the plunger rod driving member 47 is an air gap provided since the components are adapted to be rotated relative to each other. The interior of the tubular formed part 43 of the non-rotating carrier is provided with a thread of a predetermined screw pitch that corresponds to the thread on the plunger rod. That is, as will be described in greater detail below, the rod is urged towards the proximal part of the device in a rotating state while the carrier remains fix. The contact point between the proximal end of the plunger rod and the plunger cap 20, is thus in the plunger-rod-rotating-state-configuration provided with means (not shown), such that the proximal end can rotate substantially without friction losses at said contact point. The carrier 41 has preferably an outer part 54 connected to an outer cover 55. In this way, the carrier 41 can effectively pick up forces acting on the proximal part of the device in the longitudinal direction thereof.

As further seen in FIG. 20, the actuation sleeve 50 of the plunger-rod-rotating-state-configuration is provided with a stopper means 51 that is adapted to cooperate with external means 42 on the outer surface of the proximal part of the plunger rod driving member 47.

When the stopper means 51 of the plunger-rod-rotating-state-configuration engages the means 42, the driving member 47 is held in a non-rotating state, and consequently, when the stopper means 51 releases the means 42, the driving member 47 is set in a rotating state. Even if not shown in FIG. 20, the stopper means 51 and the means 42 of the plunger-rod-rotating-state-configuration, can have the same appearances and functions as described in connection with the plunger-rod-non-rotating-state-configuration. Moreover, even if no actuation spring 56 is shown in FIG. 20, such a spring can naturally be present also in the plunger-rod-rotating-state-configuration.

The Delivery Device of the First Embodiment and the Function Thereof, Will Now be Explained in Detail According to a Preferred Use Thereof.

The predetermined dose is in a first dose delivery step set by the use of the dose wheel 4, with the use of which the dose is increased by predetermined equally large dose increment steps. One predetermined dose increment step, corresponds to a clock-wise rotation of the dose wheel 4 with one step, which step corresponds to a predetermined number of degrees. Thus, with each dose increment step, the dose wheel turning member 5 is turned clock-wise an additional step corresponding to said predetermined number of degrees.

So, in order to set a predetermined dose that corresponds to for instance two dose increment steps, the dose wheel turning member 5 is turned clock-wise two steps.

When the dose wheel turning member 5 is rotated, the housing member 6 and the coupling member 34 will rotate correspondingly, and hence also the inner holding means 28, 29 of the flat spiral spring 26. Also the shoulder 11 of the housing member 6 will be brought out of engagement with the corresponding means of the outer cover when the housing member 6 is rotated clock-wise.

When the coupling member 34 rotates clock-wise, the protrusions 38 will move along the bevelled edge of the recesses 36 of the plunger rod driving member 40;47, with which recesses 36 the protrusions are initially in engage with, and the coupling member will thus move towards the distal end of the delivery device 2, compress the coupling spring 32, and unlock the dose wheel from the plunger rod driving member 40;47. The flat spiral spring 26 is hereby free to wind up and accumulate energy corresponding to the rotation of the dose wheel turning member 5 the number of degrees corresponding to one clock-wise step turn. Due to the power accumulated in the compressed coupling spring 32, the coupling member 34 will now move back towards the proximal end of the delivery device 2 when the protrusions 38 climbs over the edge of the bevelled recesses 36 and lock the coupling member 34 as well as the dose wheel 4 to the plunger rod driving member 40;47, when the protrusions 38 engage the recesses 36 following the recesses it was previously in engagement with. The dose wheel turning member 5 is turned the additional and final step, whereby the above described procedure is repeated. The flat spiral spring 26 has thus after the completion of the first dose delivery step, accumulated the energy that corresponds to the rotation of the dose wheel turning member 5 the number of degrees corresponding to a two step clock-wise turn.

The delivery device 2 is now ready to deliver the predetermined dose corresponding to two dose increment steps, i.e. the delivery device 2 is now ready to be set in a medicament delivery state. This is accomplished by in a second dose delivery step, activate, i.e. pushing, the dose actuation member 44 in the direction as indicated by the arrow A in FIG. 1. When the dose actuation member 44 is activated, said member 44 will push the actuation sleeve 50 towards the distal end of the device 2, whereby the protruding stopper means 51 of the actuation sleeve 50 and the external means 42 of the plunger rod driving member 40;47 are brought out of engagement and the plunger rod driving member 40;47 is released for rotation. In an alternative embodiment, the means that releases the plunger rod driving member 40;47 for rotation can be a breath sensing means (not shown), i.e. the plunger rod driving member 40;47 is released for rotation by means of the inhalation of the user. If the delivery device 2 is intended to be used as an injection device, the pushing of the proximal end of the actuation sleeve 50 against the patient's skin at the medicament delivery site will have the same function as the dose actuation member 44.

Due to the energy accumulated in the flat spiral spring 26 in the first dose delivery step, the coupling member 34 and the plunger rod driving member 40;47 will due to the output torque of the spring 26 when said spring now is free to unwind, rotate counter clock-wise the number of degrees corresponding to the two step turn.

In the plunger-rod-non-rotating-state-configuration, the rotation of the plunger rod driving member 40 will rotate the plunger rod, and due to non-rotating interior means provided in the interior of the device that hold the plunger rod in a non-rotating state by engaging the longitudinal extending means 53 on the rod 16 so that said interior means also is adapted to travel along the longitudinal axis of the rod, the plunger rod is urged without rotation a predetermined distance towards the proximal end into the cartridge 10. The finer the pitch of grooving, i.e. the finer the screw pitch in the interior of the nut 40, i.e. the finer the pitch of grooving of the thread on the rod, the higher the force provided to the piston, when the rod in this case is urged linearly without rotation into the cartridge. Further means to bring more of spring force to an efficient output torque, is to reduce the friction between the nut and its backing support, for instance by means of low friction washer, lubricant(s) or a ball bearing or by using low friction material in the nut and/or the plunger rod.

In the plunger-rod-rotating-state-configuration, when the plunger rod driving member 47 is rotated due to the output torque of the spring 26, this will rotate also the plunger rod 16 due to the interacting of the means 52 and 53. Due to the threaded interior of the carrier 41 that engages the rod 16, said rod is further urged towards the proximal part of cartridge with a rotating movement the predetermined distance towards the proximal end into the cartridge 10. The finer the pitch of grooving, or screw pitch, in the interior of the carrier 41, i.e. the finer the pitch of grooving of the thread on the rod, the higher the force provided to the piston, when the rod in this case is urged with rotation into the cartridge. In the plunger-rod-rotating-state-configuration, all friction is substantially between the plunger rod and the interior of the part 43, i.e. the friction is reduced in the plunger-rod-rotating-state-configuration in comparison with the plunger-rod-non-rotating-state-configuration.

In any configuration, the device 2 is designed in accordance with the cartridge 10 so that the movement of the piston 22 the predetermined distance towards the proximal end of the cartridge 10, will correspond to the delivery of the dose set in the first dose delivery step corresponding to two dose increment steps. The dose wheel 4 will rotate back to its original position when the plunger rod driving member 40;47 and the coupling member 34 is rotated during medicament delivery. The device 2 is further provided with means (not shown) that will visualize the delivered dose for the user by counting down the set dose increments. The circumferential surface of for instance the housing member 6 is preferably provided with suitable numerical indicators that are visible for the user through a window (not shown) provided in the outer cover, visualizing the dose to be delivered. The window can optionally be provided with a suitable lens or the like, in order to enlarge the dose indicators for the user. Naturally, the set dose is also visual for the user through the dose window during the first dose delivery step, as for each such step, either by using one default dose setting (described below) or varying it between doses.

When the predetermined dose has been delivered and the user of the delivery device 2 releases the dose actuation member 44, the actuation sleeve 50 will, due to the power accumulated in the actuation spring 56 when the actuation sleeve is pushed towards the distal end of the device 2, move back to its original position and once again lock the plunger rod driving member 40;47 for rotation. The plunger rod 16 will stay at its current position, with its proximal end in contact with the piston 22, and the delivery device 2 is ready to be used again. If the device is used as an injection device, the removal of the device from the medicament delivery site, i.e. the injection site, will thus cause the actuation sleeve 50 to move back to its original position, and hence temporarily or permanently stop the medicament delivery, and if provided with breath sensing means in an inhaler type of device as described above, the user may simply stop his inhalation. If the cartridge is emptied before the set dose is delivered, the dose remaining to be delivered is visualized for the user.

The user of the delivery device can also release the dose actuation member (stop his inhalation, or for injectors remove the device from the injection site), during medicament delivery and hence set the delivery device in the medicament non-delivery state before the set dose has been delivered. The user can then once again activate the dose actuation member (start to inhale, or for injectors push the proximal end of the actuation sleeve against the patient's skin), whereby the set dose continues to be delivered. The procedure above can be repeated an optional number of times until the entire set dose has been delivered. This procedure may be suitable when the patient for instance is to inhale a large predetermined volume of medicament and wants to divide the medicament delivery into multiple inhalation steps, or wants to inject a predetermined volume of medicament at different injection sites.

It is also possible to provide the device with means (not shown) that sets a certain dose as a default dose value, for instance by providing at least one of the bevelled recesses 36 with a stopper means, that will prevent the protrusions 38 from slide over the recess provided with said stopper means. This will thus prevent the user from rotating the dose wheel turning member further than the number of degrees corresponding to the default dose value, when the stopper means is provided at a recess corresponding to the rotation of the dose wheel turning member the desired number of degrees.

In the embodiments wherein the delivery device 2 is provided with the second rod, as described above, this second rod can be used for, for instance, the initial priming of the delivery device by simply pushing, or screwing if provided with threaded means, the second rod towards the proximal end of the delivery device when the device is in its medicament delivery state, whereupon the force applied to the second rod acts on the plunger cap 20 and hence on the piston 22, or by rotating the housing 202 as described above. The second rod can preferably also be used for calibration and if needed to provide an additional force on the piston 22 before the actual medicament delivery procedure. This additional force can thus correspond to the force that is often required of the device to act on the piston for it to start its movement from its initial position in the cartridge, i.e. the additional force can thus correspond to the break loose force, as described by ways of introduction. The second rod can also be used for the initial mixing of two or more types of medicament components if the device is provided with a cartridge comprising for instance a multiple chamber feature.

If a third rod is provided, said third rod can be used for any of the functions as described above in connection with the second rod, i.e. priming, calibration, mixing and provide for the break loose force to be applied to the piston, wherein the second rod and the third rod, respectively are used in combination with each other. That is, the second rod can for instance be used first in order to apply the break loose force to the piston and provide for the mixing whereupon the third rod is used for the priming and calibration. The rods are thus used in a suitable order and in a suitable combination. The joint-action between the plunger rod, the second rod and the third rod thus provide for a good control of the injector/inhalator mechanisms of the delivery device.

In the currently preferred design of the present invention according to the first embodiment, the cartridge 10 is a 1.5 ml ISO standard cartridge.

The flat spiral spring 26 is in the currently preferred embodiment made of SS 2331 stainless steel, has a thickness of 0.3 mm, a width of 4.5-5.1 mm, and an arbor diameter of 11 mm. The number of coils of the flat spiral spring 26 is 9 turns.

These flat spiral spring characteristics will give rise to an output torque of the flat spiral spring 26 in the range of 40-54 Nmm, which output torque will give rise to an operating force on the piston in the order of 27-36 N, depending on the threaded configuration of the plunger rod, i.e. the predetermined pitch of grooving of the thread on the rod, in the currently preferred design 4.3 mm/turn. The flat spiral spring 26 has further preferably no stack friction and no stick-slip and thus no lubrication of the spring 26 is needed.

Moreover, in the currently preferred design, the dose increment steps are in the order of 0.01 ml per step, and it is possible to set a dose in the range of 0.01-0.1 ml. One dose increment step of 0.01 ml, corresponds to a clock-wise rotation of the dose wheel 4 with 22.5°. Thus, the minimum dose to be delivered, i.e. 0.01 ml, corresponds to a turn of the dose wheel 4 with 22.5° and the maximum dose to be delivered, 0.1 ml, corresponds to a turn of the dose wheel with 225°.

However, the user of the device can helically pull the dose setting member towards the distal end of the device during setting of the dose to be delivered, so that the shoulder 11 is brought out of engagement with the outer cover. The flat spiral spring can thus wind up a number of coils exceeding the above described in order to accumulate more energy and thus provide for a larger dose to be delivered.

Thus, in the example described above with the delivery of a dose corresponding to two dose increment steps, the dose wheel 4 is in the first dose delivery step turned clock-wise 45°. The flat spiral spring 26 thus winds up and obtain the energy that corresponds to a 45° clock-wise turn of the dose wheel turning member 5. The later counter clock-wise rotation of the plunger rod driving member 40;47 with 45° will drive the plunger rod 0.54 mm towards the proximal end into the cartridge 10. The movement of the piston 22 towards the proximal end of the cartridge 10 with a distance of 0.54 mm, will correspond to the delivery 0.02 ml of the liquid medicament.

Figure 18:
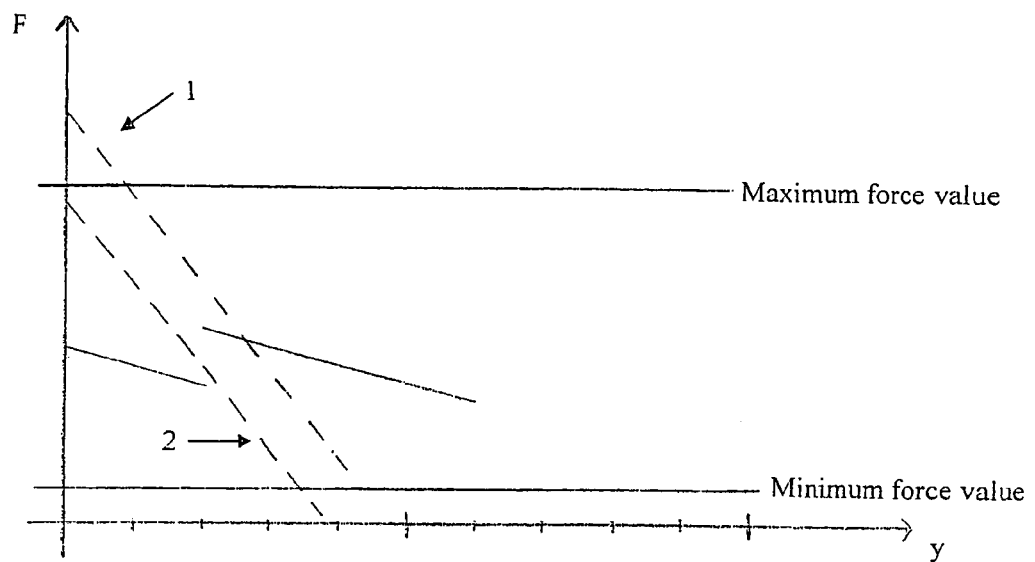
FIG. 18 illustrates graphically the force acting on the piston as a function of the travelled distance by the piston during medicament delivery in comparison with prior art devices (not to scale).

So, with the present invention according to the first embodiment, the force that drives the plunger rod with or without rotation towards the proximal end of the delivery device due to output torque of the flat spiral spring that rotates the plunger rod driving member 40, 47 is in an effective way set to a predetermined force value during the first dose delivery step, due to the interacting of the energy accumulating member and the predetermined pitch of grooving, or screw pitch, of the thread on the rod and its interacting components. This set force and the force that acts on the piston is during the entire medicament delivery ensured to be above or equal to a minimum force value, which is the lowest force value needed to deliver the set predetermined dose, and is also ensured to be below a maximum force value, which is the first force value at which it exists a risk of damaging the cartridge. FIG. 18 graphically shows the force acting on the piston (F) as a function of the travelled distance (y) by the piston from its original position during medicament delivery, wherein the delivery device first delivers a predetermined dose corresponding to two dose increment steps and thereafter delivers a dose corresponding to four dose increment steps, the indications on the y-axis thus correspond to the dose increment steps. The inclination of the continuous lines, respectively, is identical. As seen, the force is during medicament delivery above and below, respectively, said minimum and maximum force value and the force is thus within a predetermined range. It is to be understood that the force curve obtained with the inventive device according to the first embodiment can have different appearances depending on the type of spring chosen as the energy accumulating member. If for instance a substantially constant force is desired to be applied to the piston, a spiral spring resulting in such a force can easily be provided in the device by the person skilled in the art. The dashed lines 1 and 2 represent the force acting on the piston in a prior art delivery device provided with a helical spring as described by ways of introduction, during the delivery of an amount of medicament corresponding to four dose increment steps. With reference to dashed line 1, the initial force acting on the piston needs to be over the maximum force value in order for the piston to reach the distance in the cartridge that delivers a dose corresponding to four dose increments steps, i.e. there is a risk of damaging the cartridge. If the initial force is lowered, as seen when turning to the dashed line 2, the force acting on the piston will decrease to value below the minimum force value before the piston has reached its required position inside the cartridge and there is a risk that the piston will get stuck before the entire set dose is delivered. Thus, with the present invention, the predetermined dose is ensured to be delivered and the risk for damaging the cartridge or the device due to a too high initial force acting on the piston is substantially reduced, which is a problem with prior art automatic medicament delivery devices. If an additional force needs to be provided to the piston, for instance a force corresponding to the break loose force, this force can be obtained with the second rod, or the third rod, before the actual medicament delivery procedure. The application of said force can thus be carefully controlled. If the second, or third, rod is urged towards the proximal end of the device, manually by hand-force, the impact will be dampened naturally by the features of the soft-acting hand. Since the force that acts on the piston during medicament delivery is within the predetermined range independent of the amount of medicament to be delivered, the dose and the dose-to-dose accuracy are also improved in comparison with prior art automatic medicaments delivery devices. With the inventive device it is thus possible to set a predetermined dose and to target specific time limits, such as a predetermined administrating time.

Moreover, with the present invention according to the first embodiment, there is no longer a need for a pre-tensed helical spring to be provided at high tensioning in the interior of the delivery device in order to provide the plunger rod with a force for driving said rod inside the cartridge, in a way that is critical to components that are important for the dose and the dose-to-dose accuracy. Hence the problem with creep in the plastic materials of the delivery device due to tensions provided by the pre-tensed spring, as discussed above, is effectively and substantially reduced. The problem with plastic deformation is also reduced due to the fact that the force that is applied to the plunger rod does not need to be initially high as with the prior art devices, due to the effective cooperation between the energy accumulating member and the threaded plunger rod of the present invention. That is, having an output torque of a flat spiral spring rotating a plunger rod driving member and having a plunger rod provided with a thread of a predetermined screw pitch, requires less force to act on the piston in comparison with prior art devices. Particularly if friction is reduced by means of for instance low friction washers, lubricant(s), a ball bearing or by using low friction material in the plunger rod and its interacting components However, even though the present invention according to the first embodiment, has been described and illustrated in detail, said description and said illustrations shall be regarded as being non limited, since it will be appreciated that only the currently preferred embodiment has been shown. Thus the skilled person is fully capable to modify the teachings of the present invention according to the first embodiment and thus end up with for instance predetermined dose increment steps, and thus a predetermined delivery dose, in different ranges than described above, and also with different cartridge and flat spiral spring characteristics. Also, the skilled person is fully capable to replace the flat spiral spring with other types of energy accumulating members, such as other types of springs capable of providing an output torque. Moreover, the rotation directions mentioned above, can naturally be the opposite rotation direction by suitable configurations of the device that are readily carried out by the person skilled in the art, so that a counter clock-wise rotation as mentioned above instead is a clock-wise rotation, and vice versa.

The Delivery Device of the Present Invention According to a Second Embodiment

Figure 7:
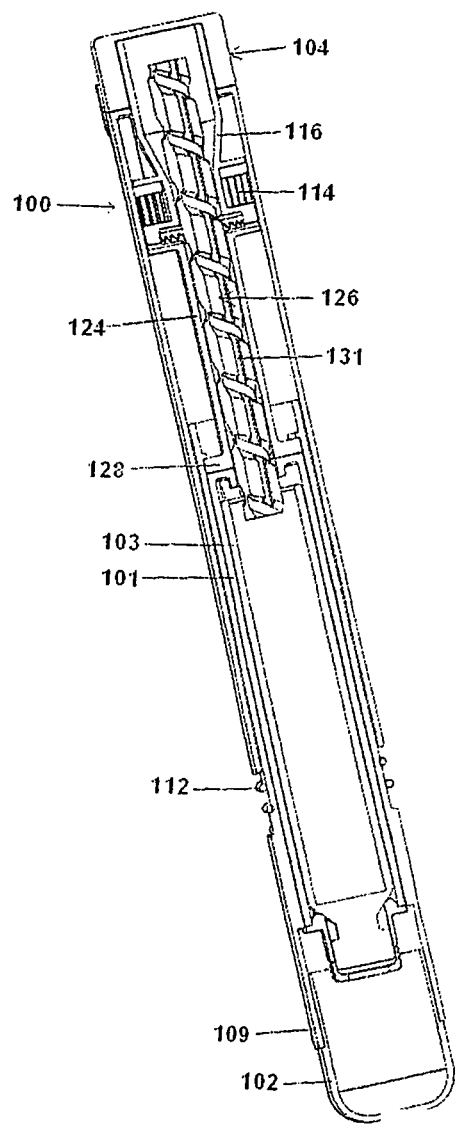
FIG. 7 illustrates the delivery device in a cross-sectional view.
Figure 8:
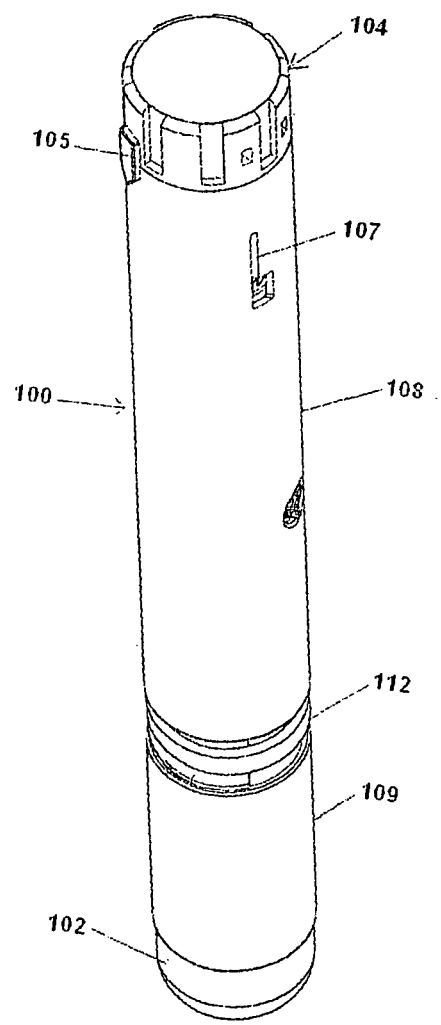
FIG. 8 illustrates an elevation view of the device.

The delivery device 100 of the second embodiment, comprises in its proximal part a cartridge housing 101 comprising a cartridge 103, as seen in FIG. 7. The cartridge 103 is intended to be filled with the liquid medicament to be administered to the patient and the delivery device is thus provided with means in order to be connected to a suitable medicament administrating member, provided with corresponding means (not shown). The medicament administrating member is in the second embodiment of the present invention preferably a needle for the injection of a liquid medicament into the body of the patient, wherein the liquid can have a low as well a high viscosity, but may also be for instance be a mouth or nasal piece, which the patient puts in his mouth or nose, respectively, whereby a metered dose of medicament is inhaled by the patient when the delivery device is set in a medicament delivery state, which will be described in further detail below. The medicament administering member can also be a member that introduces the liquid medicament to the eye of the patient, such as a suitable nozzle that sprays the medicament to the eye, or a member that introduces the medicament into the eye in the form of droplets. Naturally, a nozzle as a medicament administrating member, can also be used in order to spray the medicament onto the skin of the patient.

The delivery device 100 is further in the preferred embodiment provided with a needle shield 109, the proximal end of which extends beyond the proximal ends of the cartridge components 101, 103 in order to protect the needle. For further protection of the delivery device, said device may also in its proximal end be provided with removable cap 102. The distal end of the needle shield is provided with inward protruding stopper means 111, the function of which will be described in further detail below. The needle shield is further in its distal end provided with a helical needle shield spring 112, said spring 112 being comprised between the needle shield 109 and an outer device cover 108.

The delivery device comprises further in its distal end, a dose setting member in the form of a dose wheel turning member 104 connected to a member 116 housing an energy accumulating member. The turning member 104 is further provided with a dose indicating member 105, the function of which is to point out the set dose/dose to be delivered (as described in further detail below). The set dose/dose to be delivered is preferably provided as numerical indicators (not shown) printed on the outer cover 108.

The housing member 116 is adapted to house an energy accumulating member in the form of a flat spiral spring 114, said flat spiral spring being provided winded in layers around the housing member. The flat spiral spring is in its inner end provided with inner holding means (not shown) in order to be attached to the housing member 116, such as for instance a protruding member of the flat spiral spring adapted to be fitted with a corresponding slit in the housing member 116 or alternatively a hole of a suitable size in the flat spiral spring, and a smaller screw or other similar means for the anchoring of the flat spiral spring in the housing member 116.

At the outer end of the flat spiral spring 114, said flat spiral spring is provided with outer holding means (not shown) in order to be connected to the outer cover 108 of the delivery device 100. Said outer holding means comprises preferably a slit 107 in the outer cover 108, which engage corresponding means of the end of the flat spiral spring.

Figure 9:
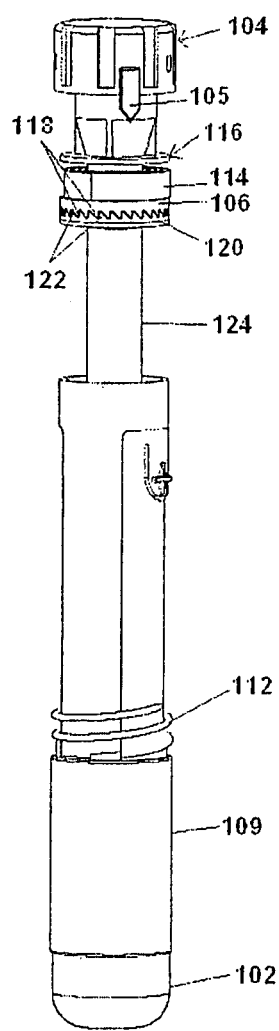
FIG. 9 illustrates the delivery device as described in connection to FIG. 8 but without the outer cover.

As seen in FIG. 9, the housing member 116 is further in its proximal end provided with a crown 106 with a number of equally distributed bevelled protrusions 118. Said protrusions 118 thus protrude towards the proximal end of the device.

The protrusions 118 of the crown 116 is adapted to be in contact with protruding bevelled teeth 122 provided equally along the circumference of a rotatable first wheel 120, said teeth 122 thus protrude towards the distal end of the device. The wheel 120 is adapted to be screw threaded on a threaded elongated plunger rod 126 which runs in the interior of the device along the longitudinal axis of said device. The proximal end of the plunger rod 126 is in contact with a piston (not shown) provided sealingly and slidably in the cartridge.

Figure 10:
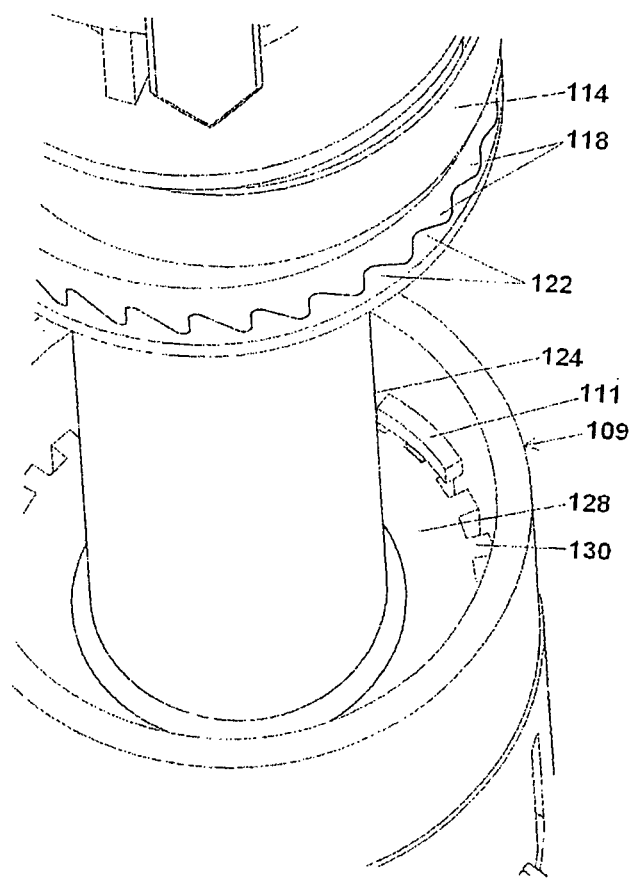
FIG. 10 illustrates an enlarged view of the connection between the needle shield and the plunger rod driving member when the device is in a medicament non-delivery state.

The wheel 120 is connected to a plunger rod driving member in the form of a second wheel 128 via a tubing 124, such that the second wheel 128 is provided proximal to the wheel 120. The second wheel 128 is thus also adapted to be screw threaded on the plunger rod, which is provided in the interior of the tubing 124. The interior of the wheels 120, 128 are thus provided with grooves of a predetermined pitch, i.e. a predetermined screw pitch, that corresponds to the thread of the plunger rod. The interior of the tubing 124 is provided with means in order to house the screw threaded plunger rod. The second wheel 128 is provided with outwardly protruding flanges 130. The flanges 130 are adapted to engage the needle shield stopper means 111, such that a stopper means 111 is provided in between two protruding flanges 130 holding the second wheel 128 in a non-rotating state when the delivery device 100 is in a non-medicament delivery state (FIG. 10) which will be described in further detail below.

Also the device of the second embodiment is adapted to be in a plunger-rod-rotating-state-configuration, wherein the plunger rod is urged towards the proximal end of the cartridge with a rotating movement. Hence, the above described refers to a configuration, wherein the plunger rod is adapted to be in a non-rotating state during medicament delivery. However, as in the first embodiment of the delivery device, the two configurations coincide in most of their respects, wherein the main difference between said configurations is within the plunger rod driving member. This will not be described in further detail below since having the teaching above referring to the plunger-rod-rotating-state-configuration of the first embodiment at hand, the skilled person can readily accomplish such a configuration also of the second embodiment, i.e. providing the interior of the wheels 120 and 128 with interior means that rotate the plunger rod, see means 52 of the first embodiment, and providing a non-rotating carrier in the interior of the device, which carrier is provided with an interior thread that corresponds to the thread on the plunger rod, see member 41 of the first embodiment.

The plunger rod 126 can be provided as a hollow member or a solid member. In the embodiment, wherein the plunger rod is provided as a hollow member, a second rod 200 can be provided inside the hollow plunger rod, extending along the longitudinal axis of said rod. Said second rod 200 can be a hollow member or a solid member as well. In the embodiment, wherein the plunger rod 126 is provided as a solid member, this second rod 200 can be provided so that its proximal end is in contact with the distal end of the plunger rod. In any case, the distal end of the second rod, preferably extends beyond the distal end of the device, which distal end of the device 100 thus is provided with an opening (not shown) in order to allow the second rod to extend beyond said end. The user of the device can thus manually apply a force, for instance by his hand, fingers or the like, on the distal end of the second rod 200, which thus provides for an additional force acting on the piston. This will be described in further detail below.

The distal end of the second rod 200 can also be comprised within in a rotatable second rod housing 202, as seen in FIGS. 16 and 17, respectively. The proximal end of the housing 202 is adapted to be firmly fixed, however adapted to be rotated, to the distal end of the delivery device 100. The proximal end of the housing 202 can for instance be in engagement with a corresponding groove (not shown) provided on the distal end of the device 100. A helical second rod spring 204 is provided around the distal end of the second rod. The distal end of the spring 204 is in contact with the inner surface of the distal end of the housing 202 and the proximal end of the spring 204 is in contact with a plate 206 firmly fixed to the second rod 200. The housing 204 is further provided with an inward protruding pin 208 that corresponds to a notch 210 in the plate 206.

When the housing is rotated, for instance in the direction as indicated by the arrow B in FIG. 16, the pin 208 will be provided just proximally of the notch 210, whereupon the spring 202, which prior to the rotation of the housing 202 is held in a compressed state, can expand and push the second rod towards the proximal end of the device, as seen in FIG. 17. FIGS. 16 and 17 thus illustrate a first and a second state of the second rod, respectively. The housing 202 can thereafter be pulled distally until the plate 206 is positioned distal to the pin 208, whereupon the housing is rotated until the pin 208 is in contact with the proximal surface of the plate 206. The second rod can also be provided with means (not shown) that prevents said rod from moving along its longitudinal axis and/or rotating after said rod have been urged towards the proximal end of the device. The second rod can also be provided with thread means in order to provide for a controlled movement of the rod. In FIGS. 16-17 is shown the embodiment wherein the second rod is provided in the hollow part of the plunger rod 126. However, it is to be understood that the proximal end of the second rod just as well can be in contact with the distal end of the plunger rod 126 as described above.

Optionally, a third rod, provided as solid or hollow member, can be provided in the delivery device, connected to the second rod with any of the means described above in connection with the coupling between the second rod and the plunger rod. The third rod can be provided with a rotating or linear moving locking mechanism or a threaded means, as described above in connection with the second rod. The function of the said third rod will be described below.

The Inventive Delivery Device of the Second Embodiment and the Function Thereof, Will Now be Explained in Detail According to a Preferred Use Thereof.

Before use, the cap 102 is removed from the device 100 and a suitable medicament administrating member is attached to the cartridge retainer, preferably a needle. Then the dose is set in a first dose delivery step by rotating the dose wheel turning member 104 in clock-wise direction with predetermined equally large dose increment steps. When the turning member is rotated, the housing member 116 rotates as well, whereupon the protrusions 118 slide over the bevelled teeth 122 of the first wheel 120, i.e. when the turning member is rotated a protrusion 118 comes in engagement with the tooth that follows the tooth that said protrusion was previously in engagement with. Each time a protrusion 118 slides over a tooth 122, the dose is increased by one step and the increase of the dose with one step corresponds to a clock-wise rotation of the turning member with a predetermined number of degrees. The set dose is indicated for the user by means of the dose indicating member 105, which points out the set dose, provided printed as numerical indicators printed along the circumference of the exterior surface of the outer cover 108, as described above.

Each time the housing member is rotated clock-wise by one step, the flat spiral spring 114, winds up and accumulates energy that corresponds to the rotation of the dose wheel turning member 104 the number of degrees that corresponds to one clock-wise step turn.

It is also possible to provide the device with means (not shown) that sets a certain dose as a default dose value, for instance by providing the exterior surface of the outer cover with a stopper means at the numerical indicator corresponding to the default dose value, which stopper means will engage the dose indicating member 105, which thus prevents the user to rotate the dose wheel turning member 104 further than the number of degrees corresponding to the default dose value.

If the delivery device needs to be reset, for instance if the user by mistake sets a too high dose, this is accomplished by pulling the dose wheel turning member 104 towards the distal end of the device, such that the protrusions 118 will be brought out of engagement with the first wheel 120, whereby the dose wheel turning member can be rotated back.

Figure 11:
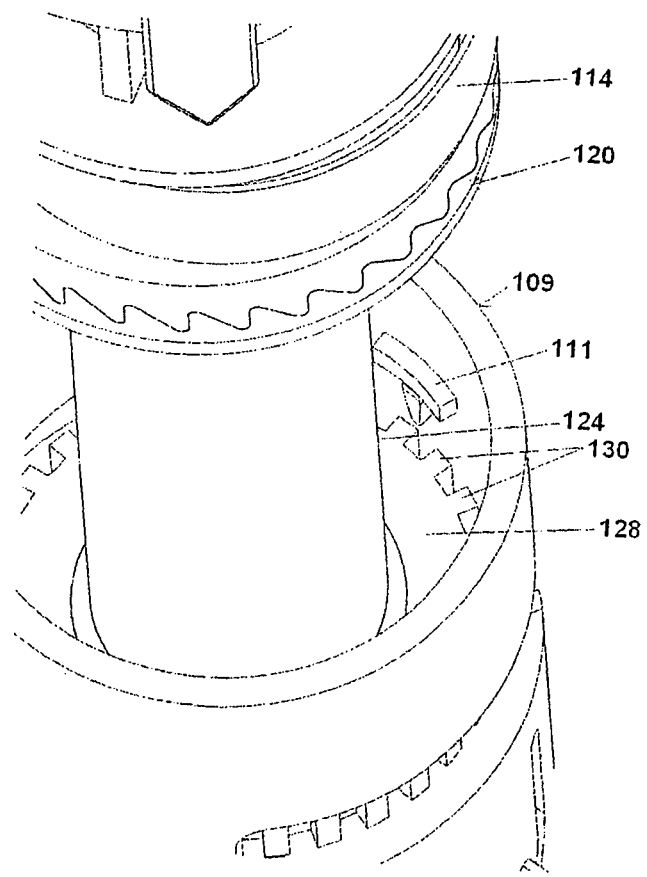
FIG. 11 illustrates an enlarged view as described in connection to FIG. 10 but when the device is in a medicament delivery state, FIGS. 12-15 and 19 refer to the delivery device according to a third embodiment.

The delivery device 100 is now ready to in a second dose delivery step be set in a medicament delivery state. This is accomplished by pushing the needle shield 109 towards the distal end of the delivery device, preferably by pushing the proximal end of the needle shield against the patient's skin at the medicament delivery site. When the needle shield moves towards the distal end of the delivery device, the stopper means 111 of the needle shield comes out of engagement with the flanges 130 of the second wheel 128, as seen in FIG. 11, which will not only set the second wheel 128 in a rotatable state but also the first wheel 120, since the wheels 120, 128 are connected via the tubing 124, as described above.

The energy accumulated in the flat spiral spring 114 in the first dose delivery step, will now due to the output torque of the spring 114 when said spring now is free to unwind, rotate the housing member 116 counter clock-wise and also the wheels 120, 128 due to the acting of the protrusions 118 on the teeth 122.

In the plunger-rod-non-rotating-state-configuration, the rotation of the wheels 120, 128 will rotate the plunger rod, and due to non-rotating interior means provided in the interior of the device that hold the plunger rod in a non-rotating state by engaging longitudinal extending means 131 on the rod 126 so that said interior means also is adapted to travel along the longitudinal axis of the rod, the plunger rod 126 is further urged without rotation a predetermined distance towards the proximal end into the cartridge 10. The finer the pitch of grooving, or screw pitch, in the interior of the wheels, i.e. the finer the pitch of grooving of the thread on the rod, the higher the force provided to the piston, when the rod in this case is urged linearly without rotation into the cartridge.

In the plunger-rod-rotating-state-configuration of the second embodiment mentioned above, the rod is urged the predetermined distance towards the proximal end of the cartridge with a rotating movement, with the finer the pitch of grooving of the thread on the rod the higher the force provided to the piston, when the rod in this case is urged with rotation into the cartridge.

Since the proximal end of the plunger rod in any configuration is in contact with the piston sealingly provided inside the cartridge, said piston will move a predetermined distance towards the proximal end of the cartridge and deliver the set volume dose. The device 100 is designed in accordance with the cartridge 103 so that the movement of the piston the predetermined distance towards the proximal end of the cartridge 103, will correspond to the delivery of the dose set in the first dose delivery step corresponding to the set dose.

The housing member and the dose wheel turning member will thus rotate back to its original position when the dose is delivered, whereupon the dose indicating member points out the dose to be delivered. If the cartridge is emptied before the entire dose is delivered, the dose remaining to be taken is pointed out by means of the dose indicating member.

When the dose has been delivered the user releases the needle shield 109, by simply removing the device from the injection site, whereupon the needle shield will move back towards the proximal end of the delivery device by means of the spring force accumulated in the needle shield spring 112 when the needle shield was pressed towards the distal end of the device. The stopper means 111 will now once again engage the flanges 130 of the second wheel 128, which thus sets the delivery device in a non-medicament delivery state, i.e. a non-rotating state of the wheels 120, 128. The plunger rod 126 will stay at its current position, with its proximal end in contact with the piston, and the delivery device 100 is ready to be used again. Preferably the needle is removed and the cap 102 is put back on after use.

The user of the delivery device can also release the needle shield during medicament delivery and hence set the delivery device in the medicament non-delivery state before the set dose has been delivered. The user can then once again push the needle shield towards the distal end of the device, whereby the set dose continues to be delivered. The procedure above can be repeated an optional number of times until the entire set dose has been delivered. This procedure is for instance suitable when a predetermined dose of medicament is to be delivered to a patient at multiple injection sites, whereby the user of the device moves the device from one injection site to another while the delivery device is in the medicament non-delivery state. If the delivery device is used as an inhaler type of device, this procedure is likewise applicable in order to divide the dose of medicament to be inhaled in multiple inhalation steps, as described above in connection with the first embodiment.

If the delivery device 100 needs to be primed before use, this is easily accomplished by setting a small dose volume to be delivered before the first dose delivery step and gently push the needle shield 109 back until a small drop is seen by the end of the needle or a small jet is ejected there from.

If the delivery device 100 is used with a medicament administrating member in the form of a mouth/nasal piece, the function of the needle shield 109 that holds and sets the wheels 120, 128 in a non-rotating and a rotating state, respectively, can be replaced with other suitable means. Such as for instance the dose actuation member 44 described in connection with the first embodiment, that when actuated will release the wheels 120, 128 for rotation. Thus, such a dose actuation member is also provided with stopper means 111 with the above described function. If the device is used as an inhaler device, the means that releases the wheels 120, 128 for rotation can be a breath sensing means, i.e. the wheel are released for rotation by means of the inhalation of the user.

In the embodiments wherein the delivery device 100 is provided with the second rod, as described above, this second rod can alternatively be used for the initial priming of the delivery device by simply pushing, or screwing if provided with threaded means, the second rod towards the proximal end of the delivery device, or by rotating the housing 202 as described above, when the device is in its medicament delivery state, whereupon the force applied to the second rod acts on the piston. The second rod can preferably also be used for calibration and if needed to provide an additional force on the piston before the actual medicament delivery procedure. This additional force can thus correspond to the force that is often required of the device to act on the piston for it to start its movement from its initial position in the cartridge, i.e. the additional force can thus correspond to the break loose force, as described by ways of introduction. The second rod can also be used for the initial mixing of two or more types of medicament components if the device is provided with a cartridge comprising for instance a multiple chamber feature.

If a third rod is provided, said third rod can be used for any of the functions as described above in connection with the second rod, i.e. priming, calibration, mixing and provide for the break loose force to be applied to the piston, wherein the second rod and the third rod, respectively are used in combination with each other. That is, the second rod can for instance be used first in order to apply the break loose force to the piston and provide for the mixing whereupon the third rod is used for the priming and calibration. The rods are thus used in a suitable order and in a suitable combination. The joint-action between the plunger rod, the second rod and the third rod thus provide for a good control of the injector/inhalator mechanisms of the delivery device.

So, with the present invention according to the second embodiment, the force that drives the plunger rod linearly with or without rotation towards the proximal end of the delivery device due to output torque of the flat spiral spring that rotates the plunger rod driving member 128, is in an effective way set to a predetermined force value during the first dose delivery step due to the interacting of the energy accumulating member and the predetermined pitch of grooving, or screw pitch, of the thread on the rod and its interacting components. This set force and the force that acts on the piston is during the entire medicament delivery by design and dimensioning ensured to be above or equal to a minimum force value, which is the lowest force value needed to deliver the set predetermined dose, and is also ensured to be below a maximum force value, which is the first force value at which it exists a risk of damaging the cartridge. FIG. 18 graphically shows the force acting on the piston (F) as a function of the travelled distance (y) by the piston from its original position during medicament delivery, wherein the delivery device first delivers a predetermined dose corresponding to two dose increment steps and thereafter delivers a dose corresponding to four dose increment steps, the indications on the y-axis thus correspond to the dose increment steps. The inclination of the continuous lines, respectively, is identical. As seen, the force is during medicament delivery above and below, respectively, said minimum and maximum force value and the force is thus within a predetermined range. It is to be understood that the force curve obtained with the inventive device according to the second embodiment can have different appearances depending on the type of spring chosen as the energy accumulating member. If for instance a substantially constant force is desired to be applied to the piston, a spiral spring resulting in such a force can easily be provided in the device by the person skilled in the art. The dashed lines 1 and 2 represent the force acting on the piston in a prior art delivery device provided with a helical spring as described by ways of introduction, during the delivery of an amount of medicament corresponding to four dose increment steps. With reference to dashed line 1, the initial force acting on the piston needs to be over the maximum force value in order for the piston to reach the distance in the cartridge that delivers a dose corresponding to four dose increments steps, i.e. there is a risk of damaging the cartridge. If the initial force is lowered, as seen when turning to the dashed line 2, the force acting on the piston will decrease to value below the minimum force value before the piston has reached its required position inside the cartridge and there is a risk that the piston will get stuck before the entire set dose is delivered. Thus, with the present invention, the predetermined dose is ensured to be delivered and the risk for damaging the cartridge or the device due to a too high initial force acting on the piston is substantially reduced, which is a problem with prior art automatic medicament delivery devices. If an additional force needs to be provided to the piston, for instance a force corresponding to the break loose force, this force can be obtained with the second rod, or the third rod, before the actual medicament delivery procedure. The application of said force can thus be carefully controlled. If the second, or third, rod is urged towards the proximal end of the device, manually by hand-force, the impact will be dampened naturally by the features of the soft-acting hand. Since the force that acts on the piston during medicament delivery is within the predetermined range independent of the amount of medicament to be delivered, the dose and the dose-to-dose accuracy is also improved in comparison with prior art automatic medicaments delivery devices. With the inventive device it is thus possible to set a predetermined dose and to target specific time limits, such as a predetermined administrating time.

Moreover, with the present invention according to the second embodiment, there is no longer a need for a pre-tensed helical spring to be provided at high tensioning in the interior of the delivery device in order to provide the plunger rod with a force for driving said rod in the cartridge, in a way that is critical to components that are important for the dose and the dose-to-dose accuracy. Hence, the problem with creep in the plastic materials of the delivery device due to tensions provided by the pre-tensed spring, as discussed above, is effectively and substantially reduced. The problem with plastic deformation is also reduced due to the fact that the force that is applied to the piston does not need to be initially high as with the prior art devices, due to the effective cooperation between the energy accumulating member and the threaded plunger rod of the present invention. That is, having an output torque of a flat spiral spring rotating a plunger rod driving member and having a plunger rod provided with a thread of a predetermined pitch of grooving, or screw pitch, requires less force to act on the piston in comparison with prior art devices. Particularly if friction is reduced by means of for instance low friction washers, lubricant(s), a ball bearing or by using low friction material in the plunger rod and its interacting components.

However, even though the present invention according to the second embodiment, has been described and illustrated in detail, said description and said illustrations shall be regarded as being non limited, since it will be appreciated that only the currently preferred embodiment has been shown. The skilled person is for instance fully capable to replace the flat spiral spring with other types of energy accumulating members, such as other types of springs capable of providing an output torque. Moreover, the rotation directions mentioned above, can naturally be the opposite rotation direction by suitable configurations of the device that are readily carried out by the person skilled in the art, so that a counter clock-wise rotation as mentioned above instead is a clock-wise rotation, and vice versa.

The Delivery Device of the Present Invention According to a Third Embodiment The delivery device 60, comprises in its proximal part a cartridge housing 66 comprising a cartridge 69. The cartridge 69 is intended to be filled with the liquid medicament to be administered to the patient and the delivery device is thus provided with means in order to be connected to a suitable medicament administrating member, provided with corresponding means (not shown). The medicament administrating member is in the third embodiment of the present invention preferably a needle for the injection of a liquid medicament into the body of the patient, wherein the liquid can have a low as well a high viscosity, but can also be for instance be a mouth or nasal piece, which the patient puts in his mouth or nose, respectively, whereby a metered dose of medicament is inhaled by the patient when the delivery device is set in a medicament delivery state, which will be described in further detail below. The medicament administering member can also be a member that introduces the liquid medicament to the eye of the patient, such as a suitable nozzle that sprays the medicament to the eye, or a member that introduces the medicament to the eye in the form of droplets. Naturally, a nozzle as a medicament administrating member, can also be used in order to spray the medicament onto the skin of the patient.

The delivery device 60 is further in the preferred embodiment provided with a needle shield 63, the proximal end of which extends beyond the proximal ends of the cartridge components in order to protect the needle. For further protection of the delivery device, said device may also in its proximal end be provided with removable cap 62. The distal end of the needle shield is provided with inward protruding stopper means 65, the function of which will be described in further detail below.

The distal part of the delivery device comprises a dose setting member in the form of a back cover 70 provided with a dose window 72. In the interior distal part of the back cover is a hollow drum 76 arranged. The drum 76 is provided with a through going slot 75 arranged in a helical-formed pattern along the surface of the drum. The back cover is further in its distal part provided with a inward protruding pin (not shown) arranged to engage and run along the slot 75 of the drum. Moreover, the external surface of the drum is circumferentially provided with for instance numerical indicators 77 which are visible for the user through a dose window 72, as described further below. The window 72 can optionally be provided with a suitable lens or the like, in order to enlarge the dose indicators for the user.

The interior surface of the back cover is provided with a thread 78 in order to be screw threaded on the proximal part of the device. The exterior surface of the proximal part of the device is thus also provided with a thread 79 that is adapted to engage the thread 78. The helical-formed configuration of the slot 75 in the drum 76 consequently corresponds to the pitch of grooving, or screw pitch, of the threads 78, 79. The thread 78 is further provided with equally distributed recesses 80, that correspond to at least one protrusion 81 on the exterior of the proximal part of the device. Alternatively, an interface (not shown) is provided between the proximal part and the distal part of the device that is provided with means that have the function of the recesses 80 and protrusions 81, see further description of said function below.

A screw threaded elongated plunger rod 84 is provided in the interior of the delivery device, running along the longitudinal axis of said device. The proximal end of the plunger rod is in contact with a piston (not shown) sealingly and slidably provided inside the cartridge 69. The plunger rod 84 is provided as a hollow member and the hollow interior of the plunger rod is provided with an energy accumulating member in the form of a helical plunger rod spring 86. The distal end of the helical spring 86 is in contact with the inner distal end of the back cover 70 and the proximal end preferably against the inner proximal end surface of the plunger rod 84. The plunger rod 84 is further connected to the drum 76 by means of inner connecting means 74.

Figure 14:
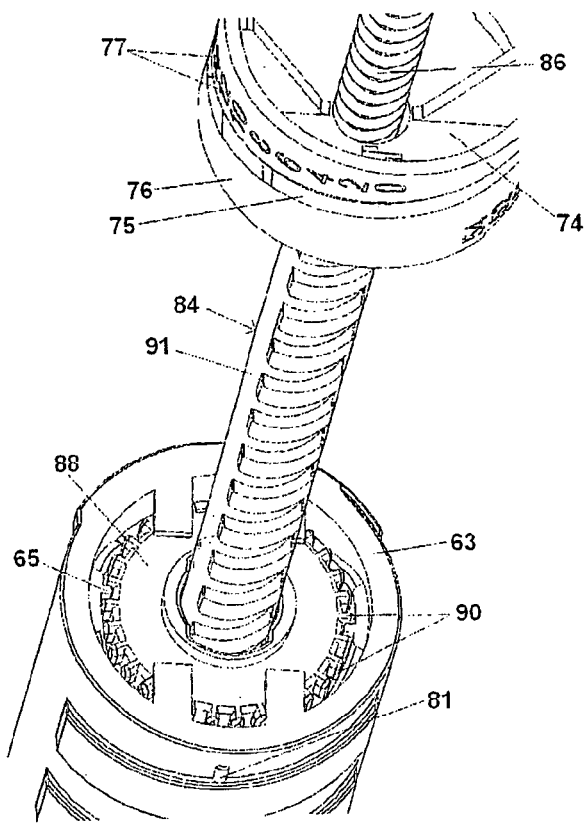
FIG. 14 illustrates in its lower part an enlarged view of the connection between the needle shield and the wheel when the device is in a medicament non-delivery state, and in its upper part an enlarged view of the dose setting member leaving out the back cover.
Figure 19:
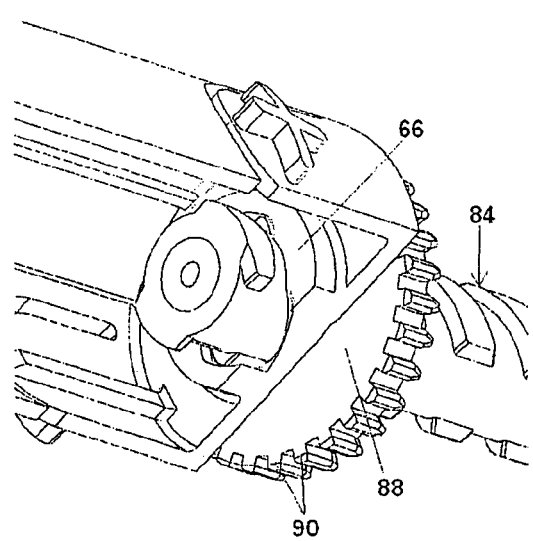
FIG. 19 illustrates an enlarged view of the connection between the plunger rod, the cartridge housing and the wheel.

The plunger rod 84 is adapted to be screwed into the cartridge housing 66 and is further adapted to be housed within a wheel 88 that is provided in the interior of the device 60 distal to the distal end of the cartridge housing, see FIG. 19. The interior part of the cartridge housing 66 that constitutes an entrance for, and is adapted to engage, the plunger rod is thus provided with a thread that has a pitch of grooving, i.e. a screw pitch, that corresponds to thread of the plunger rod. The threads 78 and 79, the thread in the interior of the cartridge housing, the thread of the plunger rod and as a logical consequence the helical formed configuration of the slot 75, all have the same predetermined pitch of grooving, or screw pitch. The wheel 88 is adapted to be in rotating state and in a non-rotating state and is therefore provided with protruding teeth 90, which teeth are adapted to engage the stopper means 65 of the needle shield 63. That is, when the delivery device 60 of the third embodiment is in a non-medicament delivery state, as seen in FIG. 14, a stopper means 65 is provided in between two protruding teeth 90, holding the wheel in a non-rotating state, as will be described in further detail below. The interior of the wheel 88 is further provided with means that corresponds to the thread on the plunger rod, so that when the wheel 88 is in the non-rotating state, the plunger rod is prevented from rotating. Thus, when the wheel 88 is released for rotation, the plunger can be rotated and screwed into the cartridge housing. The means in the interior of the wheel 88, is thus also adapted so that the wheel can travel along the longitudinal axis of the plunger rod. The interior of the wheel is thus provided with inwardly protruding means 92 that engages longitudinal extending means 91 on the plunger rod.

The device 60 can be provided with a second rod 200, which can be a hollow or a solid member, extending along the longitudinal axis of the device. The second rod is arranged so that its proximal end is in contact with the distal end of the plunger rod 84, or alternatively the second rod can be provided in the interior of the plunger rod and thus be provided inside the spring 86. The distal end of the second rod preferably extends beyond the distal end of the device, which thus is provided with an opening (not shown) in order to allow the second rod to extend beyond said end. The user of the device can thus manually apply a force, for instance by his hand, fingers or the like, on the distal end of the second rod 200, which thus provides for an additional force acting on the piston. This will be described in further detail below.

The distal end of the second rod 200 can also be comprised within in a rotatable second rod housing 202, as seen in FIGS. 16 and 17, respectively. The proximal end of the housing 202 is adapted to be firmly fixed, however adapted to be rotated, to the distal end of the delivery device 60. The proximal end of the housing 202 can for instance be in engagement with a corresponding groove (not shown) provided on the distal end of the device 60. A helical second rod spring 204 is provided around the distal end of the second rod. The distal end of the spring 204 is in contact with the inner surface of the distal end of the housing 202 and the proximal end of the spring 204 is in contact with a plate 206 firmly fixed to the second rod 200. The housing 204 is further provided with an inward protruding pin 208 that corresponds to a notch 210 in the plate 206.

When the housing is rotated, for instance in the direction as indicated by the arrow B in FIG. 16, the pin 208 will be provided just proximally of the notch 210, whereupon the spring 202, which prior to the rotation of the housing 202 is held in a compressed state, can expand and push the second rod towards the proximal end of the device, as seen in FIG. 17. FIGS. 16 and 17 thus illustrate a first and a second state of the second rod, respectively. The housing 202 can thereafter be pulled distally until the plate 206 is positioned distal to the pin 208, whereupon the housing is rotated until the pin 208 is in contact with the proximal surface of the plate 206. The second rod can also be provided with means (not shown) that prevents said rod from moving along its longitudinal axis and/or rotating after said rod have been urged towards the proximal end of the device. The second rod can also be provided with thread means in order to provide for a controlled movement of the rod. In FIGS. 16-17 is shown an embodiment wherein the second rod is provided in the interior of a hollow plunger rod. However, it is to be understood that the proximal end of the second rod just as well can be in contact with the distal end of the plunger rod 84, as is well functionable with the device according to the third embodiment.

Optionally, a third rod, provided as solid or hollow member, can be provided in the delivery device, connected to the second rod with any of the means described above in connection with the coupling between the second rod and the plunger rod. The third rod can be provided with a rotating or linear moving locking mechanism or a threaded means, as described above in connection with the second rod. The function of the said third rod will be described below.

The Inventive Delivery Device of the Third Embodiment and the Function Thereof, Will Now be Explained in Detail According to a Preferred Use Thereof.

Before use, the cap 62 is removed from the device 60 and a suitable medicament administrating member is attached to the cartridge retainer, preferably a needle. Then the dose is set in a first dose delivery step by rotating the back cover 70 clock-wise. When rotating the back-cover, the pin will run along the slot 75 of the drum 76, and the entire back cover will rotatingly move towards the proximal end of the device 60 as the thread 78 is in engagement with the thread 79. As the back cover 70 move towards the proximal end of the device, the recesses 80 of the thread 78 slide over the corresponding protrusions 81. Each time a recess 80 slides over such a corresponding protrusion 81, the dose is increased by one step and the set dose is visible for the user of the device through the dose window 72 by the numerical indicators provide on the drum 76. If the dose is set to high, the user can easily rotate the back cover counter-clock wise and adjust the set dose. It is also possible to provide the device with means (not shown) that sets a certain dose as a default dose value, for instance by providing the slot in the drum with a stopper means at a predetermined position that prevents the pin from running along said slot a longer distance than the distance that correspond to the default dose.

As the back cover moves in steps towards the proximal end of the device 60, also the plunger rod spring 86 in the interior of the plunger rod 84 is compressed and step-wise accumulates a spring force corresponding to the predetermined distance that the back cover 70 moves towards the proximal end of the device 60. The higher dose set, the greater spring force accumulated in the spring 86.

Figure 15:
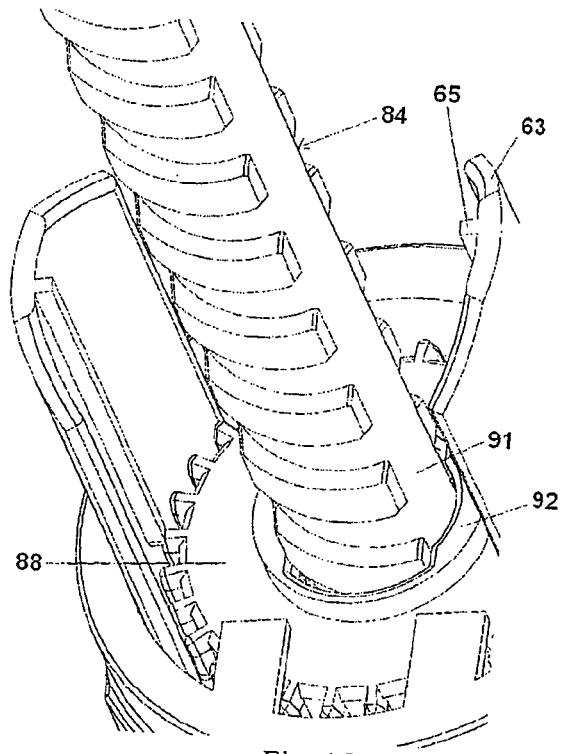
FIG. 15 illustrates an enlarged view of the connection between the needle shield and the wheel when the delivery device is in a medicament delivery state.

The delivery device 60 is now ready to in a second dose delivery step be set in a medicament delivery state. This is accomplished by pushing the needle shield 63 towards the distal end of the delivery device, preferably by pushing the proximal end of the needle shield 63 against the patient's skin at the medicament delivery site. When the needle shield moves towards the distal end of the delivery device, the stopper means 65 of the needle shield come out of engagement with the teeth 90 of the wheel 88, as seen in FIG. 15. Due to the accumulated spring force in the plunger rod spring 86 during the first dose delivery step, the plunger rod will now, provided with the force from the spring 86, be screwed into the cartridge housing and moves thus towards the proximal end of the device. Since the proximal end of the plunger rod is in contact with the piston sealingly provided inside the cartridge 69, said piston will move a predetermined distance towards the proximal end of the cartridge 69 and deliver the set volume dose. The predetermined distance that the piston 87 moves inside the cartridge, and thus the force acting on the piston, is determined by the spring force accumulated in the plunger rod spring when the dose is set as well as by the threaded design of the threaded components of the device, i.e. the threads 78 and 79, the thread in the interior of the cartridge housing and the thread on the plunger rod. The finer the pitch of grooving, or screw pitch, of the threaded components, the higher degree of accuracy will be achieved and the lower the force acting on the piston. The device 60 is designed in accordance with the cartridge so that the movement of the piston the predetermined distance towards the proximal end of the cartridge, will correspond to the delivery of the dose set in the first dose delivery step.

During dose delivery, when the plunger rod 84 is forced into the cartridge housing, the wheel 88 is rotated along with the rotating plunger rod and travels along its longitudinal axis. The drum 76 is rotated and moves along with the downwards rotating plunger rod due to the connecting means 74, whereupon the dose volume to be delivered is visible for the user through the dose window 72 and counts down until the entire dose is delivered. If the cartridge is emptied before the entire dose is delivered, the dose remaining to be taken is shown in the window. The back cover will however, stay at its current position and the device thus becomes shorter every time it is used. The exterior surface of the proximal part of the device, can thus be provided with further dose indicator means (not shown), that by means of the current position of the back cover indicates the remaining doses, i.e. the remaining amount of medicament, in the cartridge.

When the dose has been delivered the user releases the needle shield 63, by for instance simply removing the device from the injection site, whereupon the stopper means 65 once again will engage the teeth 90 of the wheel, which thus sets the delivery device 60 in a non-medicament delivery state. The plunger rod 84 will stay at its current position, with its proximal end in contact with the piston, and the delivery device is ready to be used again. Preferably the needle is removed and the cap 62 is put back on again after use.

The user of the delivery device can also release the needle shield during medicament delivery and hence set the delivery device in the medicament non-delivery state before the set dose has been delivered. The user can then once again push the needle shield towards the distal end of the device, whereby the set dose continues to be delivered. The procedure above can be repeated an optional number of times until the entire set dose has been delivered. This procedure is for instance suitable when a predetermined dose of medicament is to be delivered to a patient at multiple injection sites, whereby the user of the device moves the device from one injection site to another while the delivery device is in the medicament non-delivery state. If the delivery device is used as an inhaler, this procedure is likewise applicable in order to divide the dose of medicament to be inhaled in multiple inhalation steps, as described in connection with the first embodiment.

If the delivery device needs to be primed before use, this is easily accomplished by setting a small dose volume to be delivered before the first dose delivery step and gently push the needle shield back until a small drop is seen by the end of the needle or a small jet is ejected there from.

If the delivery device 60 is provided with the second rod, as described above, this second rod can be used for, for instance, the initial priming of the delivery device by simply pushing, or screwing if provided with threaded means, the second rod towards the proximal end of the delivery device when the device is in its medicament delivery state, whereupon the force applied to the second rod acts on the plunger rod 84 and hence on the piston. The second rod can preferably also be used for calibration and if needed to provide an additional force on the piston before the actual medicament delivery procedure. This additional force can thus correspond to the force that is often required of the device to act on the piston for it to start its movement from its initial position in the cartridge, i.e. the additional force can thus correspond to the break loose force, as described by ways of introduction. The second rod can also be used for the initial mixing of two or more types of medicament components if the device is provided with a cartridge comprising for instance a multiple chamber feature. If a third rod is provided, said third rod can be used for any of the functions as described above in connection with the second rod, i.e. priming, calibration, mixing and provide for the break loose force to be applied to the piston, wherein the second rod and the third rod, respectively are used in combination with each other. That is, the second rod can for instance be used first in order to apply the break loose force to the piston and provide for the mixing whereupon the third rod is used for the priming and calibration. The rods are thus used in a suitable order and in a suitable combination. The joint-action between the plunger rod, the second rod and the third rod thus provide for a good control of the injector/inhalator mechanisms of the delivery device.

If the delivery device 60 is used with a medicament administrating member in the form of a mouth/nasal piece, the function of the needle shield that holds and sets the wheel 88 in a non-rotating and a rotating state, respectively, can be replaced with other suitable means. Such as for instance the dose actuation member 44 described in connection with the first embodiment, that when actuated will release the wheel 88 for rotation, or a breath sensing means, i.e. the wheel is released for rotation by means of inhalation of the user. Thus, such a dose actuation member or breath sensing means is also provided with stopper means 65 with the above described function.

So, with the present invention according to the third embodiment, the force that drives the plunger rod towards the proximal end of the delivery device, due to the accumulated energy in the spring 86 and due to the threaded design of the threaded components of the device, is in an effective way set to a predetermined force value during the first dose delivery step. This set force and the force that acts on the piston is during the entire medicament delivery ensured to be above or equal to a minimum force value, which is the lowest force value needed to deliver the set predetermined dose, and is also ensured to be below a maximum force value, which is the first force value at which it exists a risk of damaging the cartridge or the device. Within this predetermined force range it is feasible to tune the device to specific desired administration times. The device is thus provided so that the maximum energy to be accumulated in the spring 86, in cooperation with the threaded components of the device, corresponds to a force applied to the piston that is below the maximum force value. That is to say that the device is provided with means (not shown) that prevents the user to rotate the back cover, and thus move it towards the proximal end of the device a too long distance, i.e. a distance that will accumulate an energy in the spring 86 that corresponds to a force applied to the piston that is above the maximum force value. Also, the setting of a dose corresponding to one dose increment step will accumulate energy in the spring that will provide the piston, in cooperation with the threaded components of the device, with a force that is above or equal to the minimum force value. FIG. 18 graphically shows the force acting on the piston (F) as a function of the travelled distance (y) by the piston from its original position during medicament delivery, wherein the delivery device first delivers a predetermined dose corresponding to two dose increment steps and thereafter delivers a dose corresponding to four dose increment steps, the indications on the y-axis thus correspond to the dose increment steps. The inclination of the continuous lines, respectively, is identical. As seen, the force is during medicament delivery above and below, respectively, said minimum and maximum force value and the force is thus within a predetermined range. It is to be understood that the force curve obtained with the inventive device according to the third embodiment can have different appearances depending on the type of spring chosen as the energy accumulating member. The dashed lines 1 and 2 represent the force acting on the piston in a prior art delivery device provided with a helical spring as described by ways of introduction, during the delivery of an amount of medicament corresponding to four dose increment steps. With reference to dashed line 1, the initial force acting on the piston needs to be over the maximum force value in order for the piston to reach the distance in the cartridge that delivers a dose corresponding to four dose increments steps, i.e. there is a risk of damaging the cartridge. If the initial force is lowered, as seen when turning to the dashed line 2, the force acting on the piston will decrease to value below the minimum force value before the piston has reached its required position inside the cartridge and there is a risk that the piston will get stuck before the entire set dose is delivered. Thus, with the present invention, the predetermined dose is ensured to be delivered and the risk for damaging the cartridge or the device due to a too high initial force acting on the piston is substantially reduced, which is a problem with prior art automatic medicament delivery devices. If an additional force needs to be provided to the piston, for instance a force corresponding to the break loose force, this force can be obtained with the second, or third, rod before the actual medicament delivery procedure. The application of said force can thus be carefully controlled. If the second rod, or third rod, is urged towards the proximal end of the device, manually by hand-force, the impact will be dampened naturally by the features of the soft-acting hand. Since the force that acts on the piston during medicament delivery is within the predetermined range independent of the amount of medicament to be delivered, the dose and the dose-to-dose accuracy is also improved in comparison with prior art automatic medicaments delivery devices. With the inventive device it is thus possible to set a predetermined dose and to target specific time limits, such as predetermined administrating times.

Moreover, with the present invention according to the third embodiment, the tensions resulting from the pre-tensed helical spring provided in the interior of the delivery device is restricted to act on a few components only, i.e. restricted to act in a controlled geometric area. In that way, said components or area, can be designed accordingly, so that the problem with creep can be reduced. The problem with plastic deformation of the plastic components of the device is also reduced due to the fact that the force that is applied to the piston does not need to be initially high as with the prior art devices, due to the effective cooperation between the energy accumulating member and the threaded components of the device of the present invention. That is, having a well controlled threaded design of said components that cooperates with the force from the energy accumulating member during dose delivery, requires less force to act on the piston in comparison with prior art devices.

However, even though the present invention according to the third embodiment, has been described and illustrated in detail, said description and said illustrations shall be regarded as being non limited, since it will be appreciated that only the currently preferred embodiment has been shown. For instance, the rotation directions mentioned above, can naturally be the opposite rotation direction by suitable configurations of the device that are readily carried out by the person skilled in the art, so that a counter clock-wise rotation as mentioned above instead is a clock-wise rotation, and vice versa.

The Delivery Device According to a Configuration Wherein the Dose Steps to be Delivered are Predetermined In a further configuration of the inventive delivery device, preferably applicable to the plunger-rod-rotating-state-configuration of the first embodiment, the delivery device is adapted to deliver predetermined dose steps of the medicament to be delivered, wherein said dose steps is not determined when the dose is about to be delivered but during the manufacturing of the device. This will for instance greatly reduce the risk for overdoses of the medicament. The medicament administrating member is thus in the predetermined-dose-step-configuration preferably a needle for the injection of a liquid medicament into the body of the patient. The delivery device of the further configuration will be described below with reference to FIG. 22.

Figure 22:
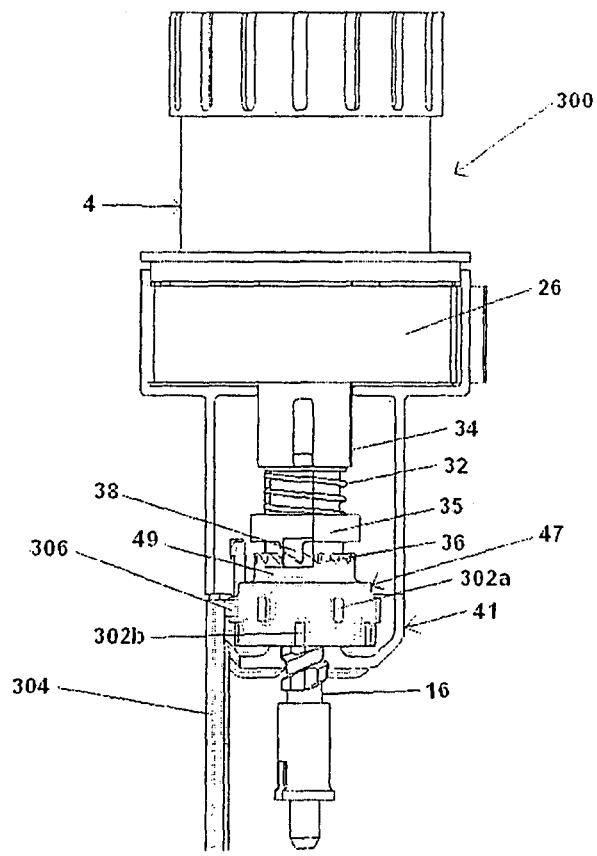
FIG. 22 illustrates a partly cross-sectional view of the distal part of the delivery device according to a configuration wherein the dose steps to be delivered are predetermined.

In FIG. 22 is shown the distal part of a delivery device 300. As the device 300 comprises substantially the same components, substantially having the same appearance and substantially cooperating in the same way as described above in connection with the first embodiment and the plunger-rod-rotating-state-configuration thereof, the interacting of said components will not be repeated herein below. The device 300 thus preferably comprises, a dose wheel 4 with a dose wheel turning member 5 and a housing member 6, housing a energy accumulating member in the form of a flat spiral spring 26. The device comprises further a threaded plunger rod 16, a coupling member 34 and a coupling spring 32, said coupling member further comprising a crown 35 with bevelled protrusions 38. As in the plunger-rod-rotating-state-configuration of the first embodiment, the device 300 comprises further a plunger rod driving member 47 provided with a skirt 49 and bevelled recesses 36 as well as a non-rotating carrier 41, provided with an interior tubular formed part 43, even if said part is not shown in FIG. 22, since it is hidden by the plunger rod driving member 47.

However, the exterior of the proximal part of the plunger rod driving member 47 is in the predetermined-dose-step-configuration provided with a number of dose step protrusions 302, equally distributed along the circumference of the proximal part of the member 47. Every other protrusion 302a is however provided a predetermined distance distal to the rest of the protrusions 302b. The protrusions 302a are thus provided equally distributed along the circumference of the member 47 with their centres provided a certain distance from the proximal end of the member 47, and the protrusions 302b are thus also provided equally distributed along the circumference of the member 47 but with their centres provided a shorter distance from the proximal end of the member 47 than the protrusions 302a. The distance between the centres of every protrusion 302 along the circumference of the driving member 47 is however equal if, as in this case, the predetermined dose steps are to be equally large, i.e. every dose step delivers the same predetermined amount of medicament.

The actuation sleeve 304 of the deliver device of the pre-determined-dose-step-configuration, is provided with an inwardly protruding stopper means 306 adapted to set the plunger rod driving member 47 in a non-rotating state as well as a rotating state. The actuation sleeve 304, and thus also the stopper means 306, is therefore adapted to be moved in the longitudinal direction of the device with a distance that corresponds to the distance between the centres of the protrusions 302a and 302b in the longitudinal direction. That is, when the stopper means 306 abuts against, as seen in FIG. 22, the right hand side of a protrusion 302, the driving member 47 is prevented to be rotated counter-clockwise, i.e. the device 300 is thus in a non-medicament delivery state.

When delivery device 300 is adapted to be used and when said device is in the non-medicament delivery device, i.e. when the plunger rod driving member is in the non-rotating state, the user rotates the dose wheel clock-wise, preferably the maximum number of steps whereby the spiral spring thus winds up an accumulates the largest permitted energy. If the stopper means abut against a protrusion 302a provided closer to the distal end of the member 47 than the protrusions 302b, the user then moves the actuation sleeve 304 and thus also the stopper means 306, the predetermined distance towards the proximal end of the device, whereby the stopper means 306 releases the plunger rod driving member 47 for rotation which sets the device in a medicament delivery state. If the stopper means 306 on the other hand abuts against a protrusion 302b, the user then instead moves the actuation sleeve 304 and thus also the stopper means 306, the predetermined distance towards the distal end of the device, whereby the stopper means 306 releases the plunger rod driving member 47 for rotation.

When the plunger rod driving member 47 is free to rotate, the output torque provided by the spring 26 will, as described above in connection with the plunger-rod-rotating-state-configuration of the first embodiment, rotate the member 47, and hence also the rod 16. However, independent of the energy accumulated in the spring 26, the member 47 will only rotate until the stopper means 306 abuts against the protrusion 302 following the protrusion 302 it previously abutted against in the direction along the circumference of the member 47, whereby the stopper means 306 travels along the circumferential surface of the member 47 the predetermined distance between the two protrusions 302a and 302b in the direction along the circumference of the member 47, each time the member is rotated.

That is, if the stopper means 306 initially abuts against the right hand side of the protrusion referred to as 302a in FIG. 22, the stopper means 306 will after the one step counter clockwise rotation of the member 47, abut against the protrusion referred to as 302b. The next time the user wants to deliver a dose, he then moves the actuation sleeve and the stopper means the predetermined distance towards the distal end of the device, whereby the member 47 rotates another step. This medicament delivery procedure can be repeated until the flat spiral spring has unwound and adapted is original non-energy accumulated state, or until the cartridge is emptied. If the former occurs before the cartridge is emptied, the user may naturally wind up the spiral spring once again. It may be that the manufacturer of the device delivers the device with the spiral spring already in a pre-tensed state, whereby the device should be used as a disposable article, i.e. when the spring has unwound it mat not be used any further.

The amount of medicament corresponding to one dose step, is thus determined by the manufacturer of the device. In the currently preferred design, the rotation of the plunger rod driving member with 30°, will correspond to the travel of the stopper means along the circumferential surface of the member 47 with a distance corresponding to the distance between a protrusion 302a and the following protrusion 302b in the direction along the circumference of the member 47, i.e. the rotation of the plunger rod driving member 47 with 30° corresponds to one dose delivery step. The rotation of the plunger rod driving member 47 with said number of degrees, corresponds to the movement of the plunger rod towards the proximal end of the cartridge with a distance of 0.3 mm which in this currently preferred design will deliver 10 μl of medicament.

As mentioned above, the distance between a protrusion 302a and a protrusion 302b in the direction along the circumference of the member 47, will determine the amount of medicament to be delivered. If said distance is equal between every protrusion, the amount of medicament will be identical in every dose step. The manufacturer of the device can however produce a device comprising a member 47 with protrusions 302, in which the distance between the protrusions in the direction along the circumference of the member is not equal everywhere. Thus, said distance can vary in correspondence with a predetermined pattern giving rise to a predetermined dose step pattern. For instance, the distance between the protrusions in the direction along the circumference of the member can become larger and larger, whereupon the amount of medicament delivered will increase for every dose step until the plunger rod driving member has completed a full turn.

As described above in connection with the first embodiment, the force applied to the piston is also in this predetermined-dose-step-configuration ensured to be with in the predetermined force range due to the cooperation between the energy accumulating member and the predetermined pitch of grooving, i.e. screw pitch, of the thread on the rod. Moreover, even if the predetermined-dose-step-configuration is described with reference to the plunger-rod-rotating-state-configuration of the first embodiment, it is to be understood that the predetermined-dose-step-configuration could be applied to a delivery device according to the first embodiment wherein the plunger rod moves towards the proximal end of the cartridge without rotation, and also with the second embodiment of the delivery device, in the plunger-rod-rotating-state-configuration as well as the plunger-rod-non-rotating-state-configuration.

2. Delivery device
4. Dose Wheel
5. Dose wheel turning member
6. Housing member
7. Splines of dose wheel turning member
8. Cartridge housing
9. Inward protruding means of housing member
10. Cartridge
11. Shoulder
13. Flat spiral spring cover
16. Plunger rod
20. Plunger cap
22. Piston
26. Flat spiral spring
28. Protruding member of flat spiral spring
29. Slit in housing member
30. Bend of flat spiral spring
31. Flat spiral spring holding means
32. Coupling spring
34. Coupling member
35. Crown of coupling member
36. Bevelled recesses of plunger rod driving member
38. Bevelled protrusions of crown
40. Plunger rod driving member
41. Non-rotating carrier
42. Plunger rod driving member flanges
43. Interior part of carrier 41
44. Dose actuation member
47. Plunger rod driving member
49. Skirt of nut
50. Actuation sleeve
51. Protruding stopper means of actuation sleeve
52. Interior means of member 47
53. Longitudinal extending means on plunger rod
54. Outer part of carrier 41
55. Outer cover
56. Actuation spring
100. Delivery device
101. Cartridge housing
102. Cap
103. Cartridge
104. Dose wheel turning member
105. Dose indicating member
106. Crown of housing member
107. Slit in outer cover
108. Outer cover
109. Needle shield
111. Needle shield stopper means
112. Needle shield spring
114. Flat spiral spring
116. Housing member
118. Protrusions of crown
120. First wheel
122. Teeth of first wheel
124. Tubing
126. Plunger rod
128. Second wheel
130. Flanges of second wheel
131. Longitudinal extending means on the rod
60. Delivery device
62. Cap
63. Needle shield
65. Needle shield stopper means
66. Cartridge housing
69. Cartridge
70. Back cover
72. Dose window
75. Slot in drum
76. Drum
77. Numerical indicators
78. Thread in back cover
79. Thread on device
80. Recesses in thread 78
81. Protrusions corresponding to recesses 80
84. Plunger rod
86. Helical plunger rod spring
87. Piston
88. Wheel
90. Teeth of wheel
91. Longitudinal extending means on the rod
92. Interior means
200. Second rod 202. Second rod housing
204. Second rod spring
206. Plate
208. Pin
210. Notch in plate
300. Delivery device
302. Dose step protrusions
304. Actuation sleeve
306. Stopper means of actuation sleeve

The invention claimed is:

1. A device for delivering predetermined doses of liquid medicament, which device is adapted to be in a medicament delivery state and in a medicament non-delivery state, comprising:
   a cartridge adapted to contain the liquid medicament and a piston sealingly and slidably arranged in the cartridge;
   an energy accumulating member;
   an elongated screw threaded plunger rod adapted to be arranged in an interior of the device, wherein a proximal end of the plunger rod is adapted to be in contact with the piston, such that, when a first force from the energy accumulating member is applied to the plunger rod when the device is in the medicament delivery state, the plunger rod and the piston move toward a proximal end of the cartridge with a predetermined distance and expel a predetermined dose of the liquid medicament from the cartridge;
   at least one additional rod that extends along a longitudinal axis of the device and that is in contact with the plunger rod, wherein a distal end of the at least one additional rod extends beyond a distal end of the device, and the at least one additional rod is adapted, upon activation, to be moved by a second force in the proximal direction of the device.

2. The device of claim 1, wherein during medicament delivery the device is adapted to be set in the medicament non-delivery state before an entire set dose has been delivered, whereupon the plunger rod stops moving toward the proximal end of the cartridge, and the device thereafter is adapted to be set in the medicament delivery state, whereupon the plunger rod continues to move the predetermined distance toward the proximal end of the device.

3. The device of claim 1, wherein the device is adapted to be connected to a medicament administering member, and the medicament administering member has a form of a mouth piece or a nasal piece that a patient can put in the patient's mouth or nose, respectively, whereby the predetermined dose of medicament is inhaled by the patient when the delivery device is in the medicament delivery state.

4. The device of claim 1, wherein the device is adapted to be connected to a medicament administering member, and the medicament administering member has a form of a nozzle, whereby the predetermined dose of medicament is sprayed into a patient's eye or onto the patient's skin when the delivery device is in the medicament delivery state.

5. The device of claim 1, wherein the device is adapted to be connected to a medicament administering member, and the medicament administering member has a form of a member that can introduce the predetermined dose of medicament into a patient's eye as at least one drop when the delivery device is in the medicament delivery state.

6. The device of claim 1, wherein the device is adapted to be connected to a medicament administering member, and the medicament administering member has a form of a needle for injecting the predetermined dose of medicament into a patient's body when the delivery device is in the medicament delivery state.

7. The device of claim 1, wherein the plunger rod is a hollow plunger rod and the at least one additional rod is disposed inside and extending along a longitudinal axis of the hollow plunger rod.

8. The device of claim 1, wherein the second force is a manual force applied to the at least one additional rod by a user.

9. The device of claim 1, wherein the second force is an accumulated force applied by a resilient device.

10. The device of claim 9, wherein a distal end of the at least one additional rod is disposed within a housing provided on a distal end of the device, the housing is adapted to be rotated to a second position from a first position, the housing comprises a helical spring in contact with the at least one additional rod, the helical spring is in a compressed state when the housing is in the first position, and the helical spring is adapted to provide, when the housing is rotated to the second position, the at least one additional rod with the second force that drives the at least one additional rod toward the proximal end of the device.

11. The device of claim 1, wherein the second force that is applied to the at least one additional rod is applied before medicament delivery and corresponds to a force needed for the piston to start moving from an initial position in a distal end of the cartridge.

12. The device of claim 11, wherein the force that is applied to the at least one additional rod is applied before medicament delivery and corresponds to a force needed for initial priming of the device, calibration of the device, or mixing of medicament in the cartridge.

13. A device for delivering predetermined doses of liquid medicament, which device is adapted to be in a medicament delivery state and in a medicament non-delivery state, comprising:
   a cartridge adapted to contain the liquid medicament and a piston sealingly and slidably arranged in the cartridge;
   an energy accumulating member;
   an elongated screw threaded plunger rod adapted to be arranged in an interior of the device, wherein a proximal end of the plunger rod is adapted to be in contact with the piston, such that, when a first force from the energy accumulating member is applied to the plunger rod when the device is in the medicament delivery state, the plunger rod and the piston move toward a proximal end of the cartridge with a predetermined distance and expel a predetermined dose of the liquid medicament from the cartridge;
   at least one additional rod that extends along a longitudinal axis of the device and that is in contact with the plunger rod, wherein a distal end of the at least one additional rod extends beyond a distal end of the device, and the at least one additional rod is adapted, upon activation, to be moved by a second force in the proximal direction of the device; and
   a dose setting member adapted to be rotated by at least one predetermined step when the device is in the medicament non-delivery state, wherein rotation of the dose setting member by one step increases a set dose by one step and also increases the accumulated energy in the energy accumulating member by one step.

14. The device of claim 13, wherein the energy accumulating member is adapted to accumulate energy in terms of at least one predetermined step when the device is in the medicament non-delivery state, which energy is adapted to be transferred to the plunger rod so that the plunger rod is provided with the force that drives the plunger rod and the piston the predetermined distance toward the proximal end of the cartridge when the device is in the medicament delivery state.

15. The device of claim 14, wherein the energy accumulating member is a spring capable of providing an output torque and the accumulated energy is energy that results from rotational tensioning of the spring, which accumulated energy is transferred to the output torque when the tensioning of the spring is released when the device is set in the medicament delivery state; the output torque is adapted to be provided to a plunger rod driving member provided with a predetermined pitch of grooving that corresponds to the threads of the plunger rod; and rotation of the plunger rod driving member due to the output torque of the spring drives the plunger rod without rotation the predetermined distance towards the proximal end of the cartridge with a predetermined force.

16. The device of claim 15, wherein the spring is a flat spiral spring.

17. The device of claim 14, wherein the energy accumulating member is a helical spring and the accumulated energy is energy that results from compression of the helical spring; the accumulated energy is adapted to be transferred to the plunger rod when the device is in the medicament delivery state, so that the plunger rod moves with rotation toward the proximal end of the cartridge the predetermined distance; and the cartridge is disposed in a cartridge housing that is provided with a thread with a predetermined pitch of grooving that corresponds to the thread of the plunger rod.

18. The device of claim 13, wherein cooperation between the predetermined energy of the energy accumulating member that is accumulated when the dose setting member is rotated and the thread on the plunger rod determines a predetermined force that is applied to the piston during medicament delivery.

19. The device of claim 13, wherein the device is adapted to be set to a default dose value to be delivered, and the dose setting member is adapted to be rotated only a predetermined number of steps that corresponds to the default dose value.

* * * * *